(12) United States Patent
Lemischka et al.

(10) Patent No.: US 7,662,941 B2
(45) Date of Patent: Feb. 16, 2010

(54) EMBRYONIC STEM CELL SELF MAINTENANCE AND RENEWAL REPORTER

(75) Inventors: Ihor R. Lemischka, Princeton, NJ (US); Christoph Schaniel, Princeton, NJ (US); Feng Li, Plainsboro, NJ (US); Xenla Schafer, Princeton, NJ (US); Patrick J. Paddison, Oyster Bay, NY (US)

(73) Assignee: The Trustees of the University of Princeton - Princeton University, Princeton, NJ (US)

( * ) Notice: Subject to any disclaimer, the term of this patent is extended or adjusted under 35 U.S.C. 154(b) by 0 days.

(21) Appl. No.: 11/332,943

(22) Filed: Jan. 17, 2006

(65) Prior Publication Data
US 2006/0195918 A1 Aug. 31, 2006

Related U.S. Application Data

(60) Provisional application No. 60/644,785, filed on Jan. 18, 2005.

(51) Int. Cl.
C07H 21/04 (2006.01)
A01N 63/00 (2006.01)
C12N 15/74 (2006.01)

(52) U.S. Cl. ............... 536/23.1; 435/320.1; 424/93.2; 424/93.21

(58) Field of Classification Search .................. None
See application file for complete search history.

(56) References Cited

U.S. PATENT DOCUMENTS

2005/0054824 A1* 3/2005 Saitou et al. ............ 530/350
2006/0064770 A1* 3/2006 Frendewey et al. ......... 800/18

OTHER PUBLICATIONS

Lin et al. p53 induces differentiation of a mouse embryonic stem cells by suppressing Nanog expression. Nature Cell Biology, 2005. 7(2) 165-171.*
Hart et al, Dev Dynamics 2004;230:187-98.*
Nanog locus, Entrez Genome database, 2008.*
Keller, "Embryonic stem cell differentiation: emergence of a new era in biology and medicine," Genes Dev 19:1129-1155 (2005).
Loebel et al., "Lineage choice and differentiation in mouse embryos and embryonic stem cells," Dev Biol. 264:1-14 (2003).
Rao, "Conserved and divergent paths that regulate self-renewal in mouse and human embryonic stem cells," Dev Bio. 275:269-286 (2004).
Mitsui et al., "The homeoprotein Nanog is required for maintenance of pluripotency in mouse epiblast and ES cells," Cell 113: 631-642 (2003).
Chambers et al., "Functional expression cloning of Nanog, a pluripotency sustaining factor in embryonic stem cells," Cell 113: 643-655 (2003).
Hatano et al., "Pluripotential competence of cells associated with Nanog activity," Mech. Dev. 122:67-79 (2005).
Yamaguchi et al., "Nanog expression in mouse germ cell development," Gene Expression Patterns 5:639-646 (2005).
Pesce et al., "In line with our ancestors: Oct. 4 and the mammalian germ," BioEssays 20:722-732 (1998).
Avilion et al., Multipotent cell lineages in early mouse development depend on SOX2 function, Genes Dev. 17:126-140 (2003).
Ivanova etal., "Dissencting self-renewal in stem cells with RNA interference," Nature 442:533-538 (2006).
Arced et al., "Mouse GATA-4: a retinoic acid-inducible GATA-binding transcription factor expressed in endodermally derived tissues and heart," Mol. Cell. Biol. 13:2235-2246 (1993).
Martin and Evans, "Differentiation of clonal lines of teratocarcinoma cells: formation of embryoid bodies in vitro," PNAS 72:1441-1445 (1975).
Doetschman et al., "The in vitro development of blastocyst-derived embryonic stem cell lines: formation of visceral yolk sac, blood islands and myocardium," J. Embryol. Exp. Morphol. 87:27-45 (1985).
Wilkinson et al., "Expression pattern of the mouse T gene and its role in mesoderm formation," Nature 343:657-658 (1990).
Mason et al., "Evidence from molecular cloning that SPARC, a major product of mouse embryo parietal endoderm, is related to an endothelial cell 'culture shock' glycoprotein of Mr 43,000," EMBO J. 5:1465-1472 (1986).
Haub and Goldfarb, "Expression of the fibroblast growth factor-5 gene in the mouse embryo," Development 112:397-406 (1991).
Hébert et al., "mRNA localization studies suggest that murine FGF-5 plays a role in —gastrulation," Development 112:407-415.
Okabe et al., "Development of neuronal precursor cells and functional postmitotic neurons from embryonic stem cells in vitro," Mech. Dev. 59:89-102 (1996).
Jirmanova et al., "Differential contributions of ERK and PI3-kinase to the regulation of cyclin D1 expression and to the control of the G1/S transition in mouse embryonic stem cells," Oncogene 21:5515-5528 (2002).
Paling et al., 2004. J. Bio. Chem. 279:48063-48070 (2004).
Aubert et al., "Functional gene screening in embryonic stem cells implicates Wnt antagonism in neural differentiation," Nat. Biotechnol. 20:1240-1245 (2002).
Ohinata et al., "Blimp1 is a critical determinant of the germ cell lineage in mice," Nature 436:207-213 (2005).
Solter and Knowles, "Monoclonal antibody defining a stage-specific mouse embryonic antigen (SSEA-1)," PNAS 75:5565-5569 (1978).
Matsui et al., "Derivation of pluripotential embryonic stem cells from murine primordial germ cells in culture," Cell 70:841-847 (1992).
Geijsen et al., "Derivation of embryonic germ cells and male gametes from embryonic stem cells," Nature 427:148-154 (2003).
Sato et al., "Identification of PGC7, a new gene expressed specifically in preimplantation embryos and germ cells," Mech Dev. 113:91-94 (2002).

(Continued)

*Primary Examiner*—Q. Janice Li
(74) *Attorney, Agent, or Firm*—Medlen & Carroll, LLP

(57) ABSTRACT

The present invention relates to methods and compositions for assaying embryonic stem cell maintenance. In particular, the present invention provides reporter constructs for stem cell pluripotency and differentiation and cells and organisms containing such constructs.

22 Claims, 25 Drawing Sheets

OTHER PUBLICATIONS

Fuhrmann et al., "Mouse germline restriction of Oct. 4 expression by germ cell nuclear factor," Dev Cell 1:377-387 (2001).

Yang et al., "Analysis of germ cell nuclear factor transcripts and protein expression during spermatogenesis," Biol Reprod. 68:1620-1630 (2003).

Youngren et al., "The Ter mutation in the dead end gene causes germ cell loss and testicular germ cell tumours," Nature 435:360-364(2005).

Rideout et al., "Nuclear cloning and epigenetic reprogramming of the genome," Science 293:1093-1098 (2001).

Bernstine et al., 1973. PNAS 70:3899-3903(1973).

Hajkova et al., "Epigenetic reprogramming in mouse primordial germ cells," Mech Dev. 117:15-23 (2002).

Hübner et al, "Derivation of oocytes from mouse embryonic stem cells," Science 300:1251-1256 (2003).

Toyooka et al., "Embryonic stem cells can form germ cells in vitro," PNAS 100:11457-11462 (2003).

Koshimizu et al., Retinoic acid is a potent growth activator of mouse primordial germ cells in vitro, Dev Bio. 168:683-685 (1995).

Dolci et al., "Requirement for mast cell growth factor for primordial germ cell survival in culture," Nature 352:809-811 (1991).

Godin et al., "Effects of the steel gene product on mouse primordial germ cells in culture," Nature. 352:807-809 (1991).

Matsui et al., "Effect of Steel factor and leukaemia inhibitory factor on murine primordial germ cells in culture," Nature 353:750-752 (1991).

Resnick et al., "Long-term proliferation of mouse primordial germ cells in culture," Nature 359:550-551 (1992).

Strumpf et al., 2005. Development 132:2093-2102 (2005).

Tada et al., "Nuclear reprogramming of somatic cells by in vitro hybridization with ES cells," Curr. Biol. 11:1553-1558 (2001).

Taranger et al., "Induction of dedifferentiation, genomewide transcriptional programming, and epigenetic reprogramming by extracts of carcinoma and embryonic stem cells.," Mol. Biol. Cell 16:5719-5739. Epub Sep. 29, 2005.

Schaniel et al., "Delivery of short hairpin RNAs—triggers of gene silencing—into mouse embryonic stem cells," Nature Methods, 3:397-400 (2006).

* cited by examiner

Figure 1
SEQ ID NO:55

GGCGCGCCccaatgtgaagagcaagcaagaaacgctgagtgctgaaaggaaagccgtgt
ataaacagagactttggcagcaaggtctgactctttcatgtctgtagaaagaatggaag
aggaaactcagatcccccacttgacctgaaacttcccactagagatcgccagggtctgg
aggtgcagccgtggttaaaagatgaataaagtgaaatgaggtaaagcctcttttcgggg
ggggggggatgtctttagatcagaggatgcccctaagcttccctccctcccagtctgg
gtcaccttacagcttcttttgcattacaatgtccatggtggaccctgcaggtgggatta
actgtgaattcacagggctggtggggcgtgggtgccgcctgggtgcctgggagaatagg
gggtgggtagggtaggaggcttgagggggaggagcaggacctacccctttaaatctatc
gccttgagccgttggcctt*CAGATAGGCTGATTTGGTTGGTGTCTTGCTCTTTCTGTGG*
*GAAGGCTGCCCGGGCCGCCACC*ATGAAAAAGCCTGAACTCACCGCGACGTCTGTCGAG
AAGTTTCTGATCGAAAAGTTCGACAGCGTCTCCGACCTGATGCAGCTCTCGGAGGGCGA
AGAATCTCGTGCTTTCAGCTTCGATGTAGGAGGGCGTGGATATGTCCTGCGGGTAAATA
GCTGCGCCGATGGTTTCTACAAAGATCGTTATGTTTATCGGCACTTTGCATCGGCCGCG
CTCCCGATTCCGGAAGTGCTTGACATTGGGGAATTCAGCGAGAGCCTGACCTATTGCAT
CTCCCGCCGTGCACAGGGTGTCACGTTGCAAGACCTGCCTGAAACCGAACTGCCCGCTG
TTCTGCAGCCGGTCGCGGAGGCCATGGATGCGATCGCTGCGGCCGATCTTAGCCAGACG
AGCGGGTTCGGCCCATTCGGACCGCAAGGAATCGGTCAATACACTACATGGCGTGATTT
CATATGCGCGATTGCTGATCCCCATGTGTATCACTGGCAAACTGTGATGGACGACACCG
TCAGTGCGTCCGTCGCGCAGGCTCTCGATGAGCTGATGCTTTGGGCCGAGGACTGCCCC
GAAGTCCGGCACCTCGTGCACGCGGATTTCGGCTCCAACAATGTCCTGACGGACAATGG
CCGCATAACAGCGGTCATTGACTGGAGCGAGGCGATGTTCGGGGATTCCCAATACGAGG
TCGCCAACATCTTCTTCTGGAGGCCGTGGTTGGCTTGTATGGAGCAGCAGACGCGCTAC
TTCGAGCGGAGGCATCCGGAGCTTGCAGGATCGCCGCGGCTCCGGGCGTATATGCTCCG
CATTGGTCTTGACCAACTCTATCAGAGCTTGGTTGACGGCAATTTCGATGATGCAGCTT
GGGCGCAGGGTCGATGCGACGCAATCGTCCGATCCGGAGCCGGGACTGTCGGGCGTACA
CAAATCGCCCGCAGAAGCGCGGCCGTCTGGACCGATGGCTGTGTAGAAGTACTCGCCGA
TAGTGGAAACCGACGCCCAGCACTCGTCCGAGGGCAAAGGAAATGGTGAGCAAGGGCG
AGGAGCTGTTCACCGGGGTGGTGCCCATCCTGGTCGAGCTGGACGGCGACGTAAACGGC
CACAAGTTCAGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCGTGACCACCC
TGACCTACGGCGTGCAGTGCTTCAGCCGCTACCCCGACCACATGAAGCAGCACGACTTC
TTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAG
TACAACTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGACCACT
ACCAGCAGAACACCCCCATCGGCGACGGCCCCGTGCTGCTGCCCGACAACCACTACCTG
AGCACCCAGTCCGCCCTGAGCAAAGACCCCAACGAGAAGCGCGATCACATGGTCCTGCT
GGAGTTCGTGACCGCCGCCGGGATCACTCTCGGCATGGACGAGCTGTACAAGTAAAGCG
GCCGCGACTCTAGATCATAATCAGCCATACCACATTTGTAGAGGTTTTACTTGCTTTAA
AAAACCTCCCACACCTCCCCCTGAACCTGAAACATAAAATGAATGCAATTGTTGTTGTT
AACTTGTTTATTGCAGCTTATAATGGTTACAAATAAAGCAATAGCATCACAAATTTCAC
AAATAAAGCATTTTTTTCACTGCATTCTAGTTGTGGTTAATTAA*GGAACGCCTCATCAA*
*TGCCTGCAGTTTTTCATCCCGAGAACTATTCTTGCTTACAAGGGTCTGCTACTGA*gatg

Figure 1 Continued

```
ctctgcacagaggctggtaaggaattcagtccccgaagaacccagtaaattagggtaag
agtagaaaaaacgggctgaagggttattgcttctttatgaaccgtagtagtcattaaca
taagcgggtgtccttatcactcttctggaaaccctctgagtttgaccggtgatacgtt
ggccttctagtctgaaatagagatccgggacacaggacggagcaatataaggctcttgt
gtgtatttgagaacctaaatatttgggctctttggaatatgttcgggggcagtgagtgg
tgtcttcagtagcagggagacctaacatcctagcttggaatgagcacccattttttg
gtgaggttatacagttagtttgcaatttgcccaaatggccgttttctccagcagaagca
gttagcatttctctcaacctttgggaatatggatgtcacttagcagttctgggtttgtg
agctcagtgctccttccaaacGGCCGGCC
```

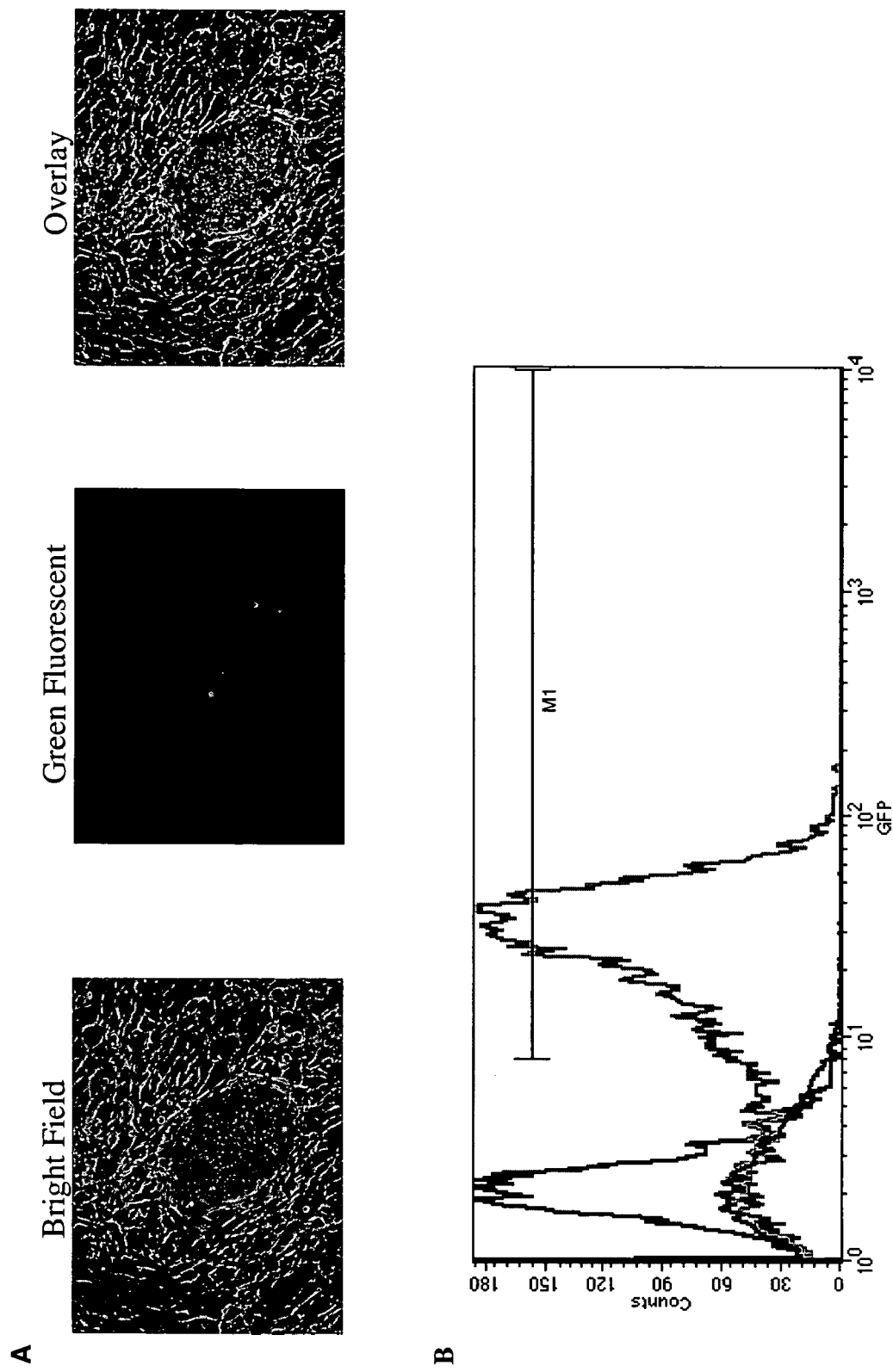

Figure 6
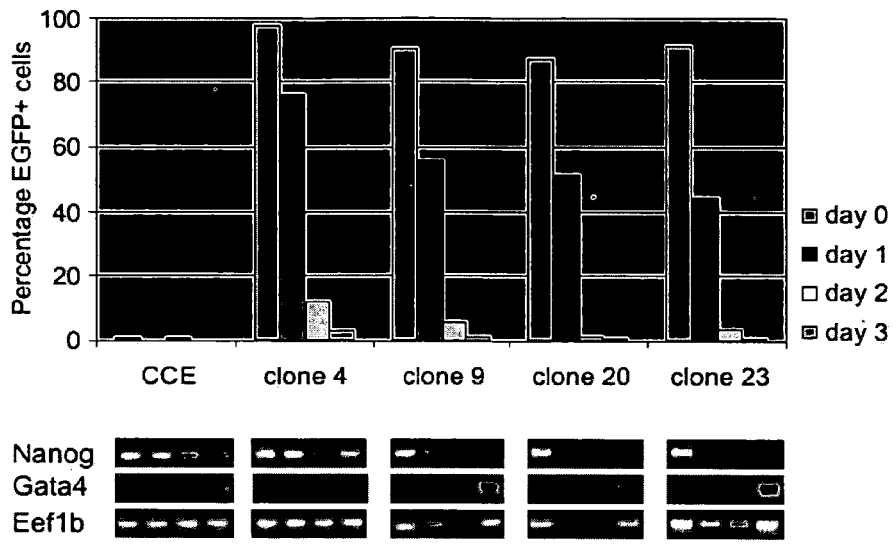
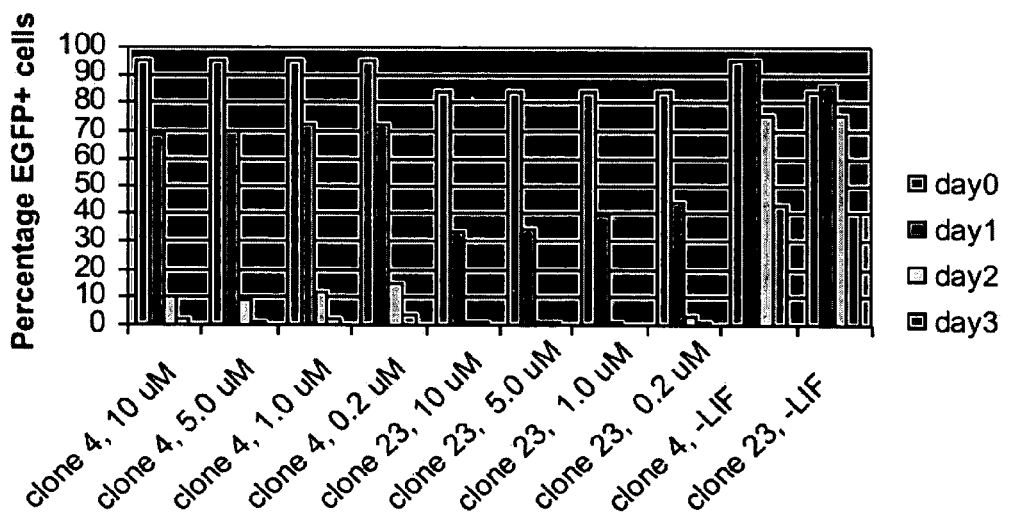

Figure 9
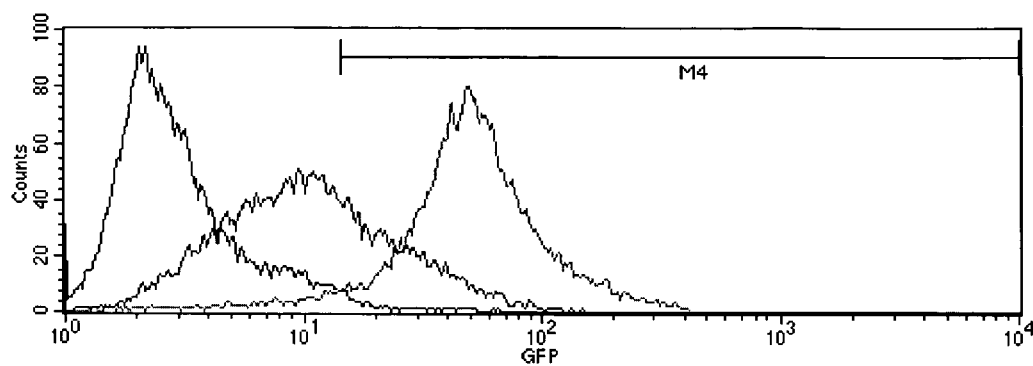
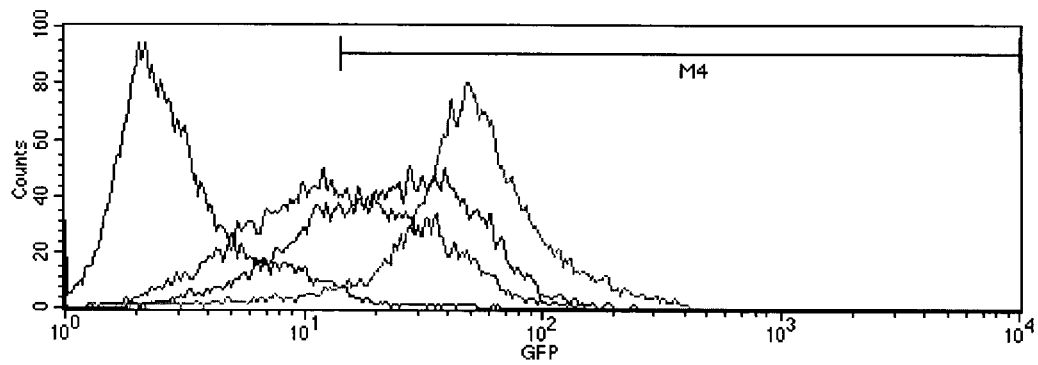

Figure 11
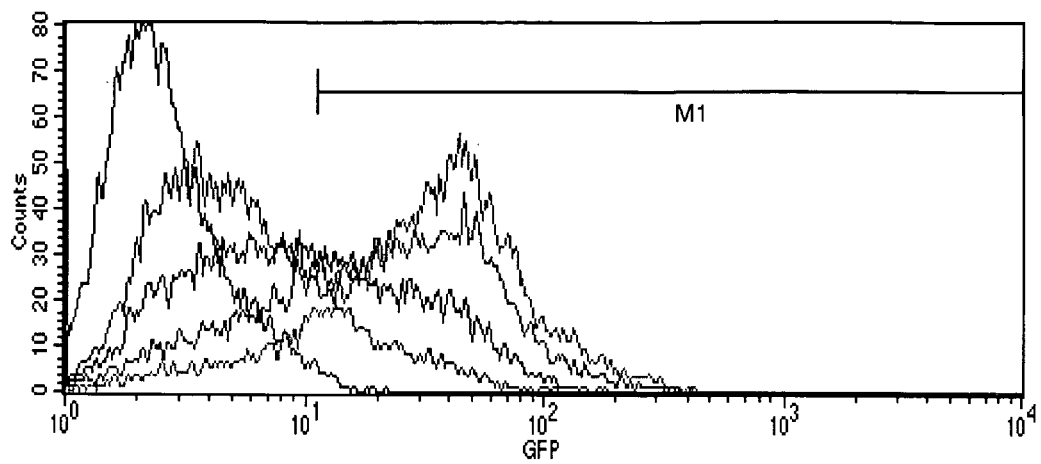
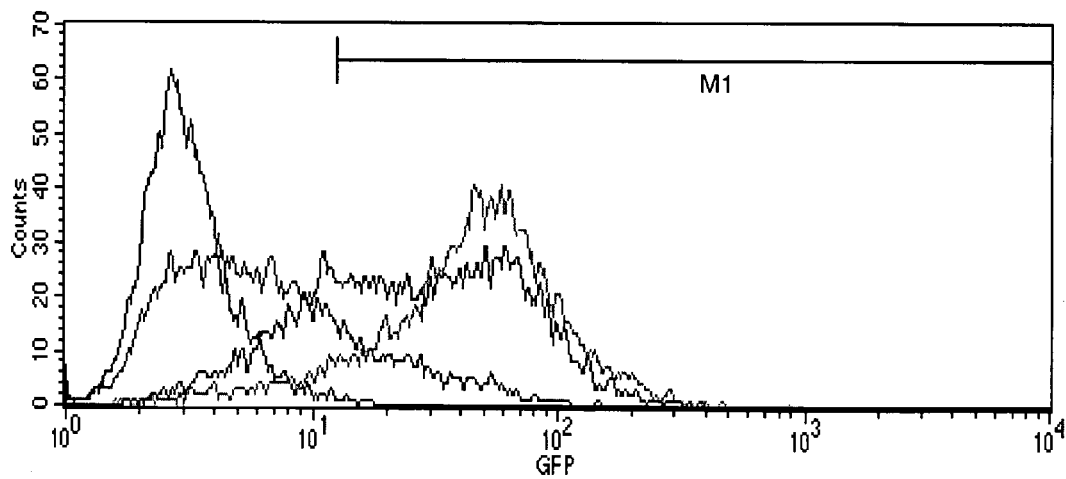

Figure 17 D
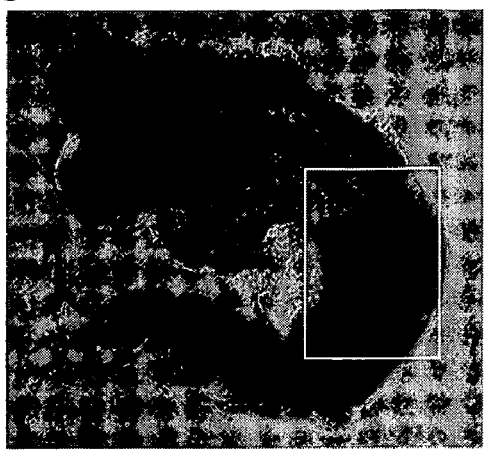
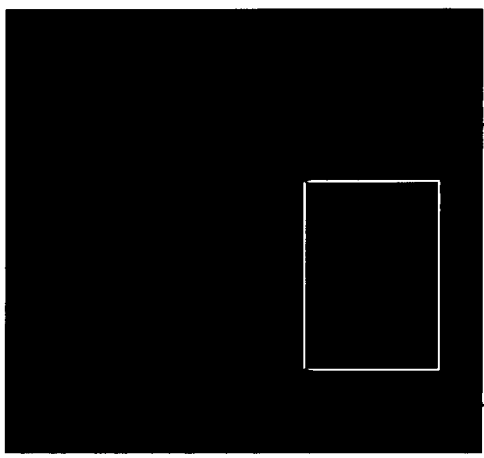
Magnification:4x　　　　　　　　　　Magnification:10x
Figure 17 E
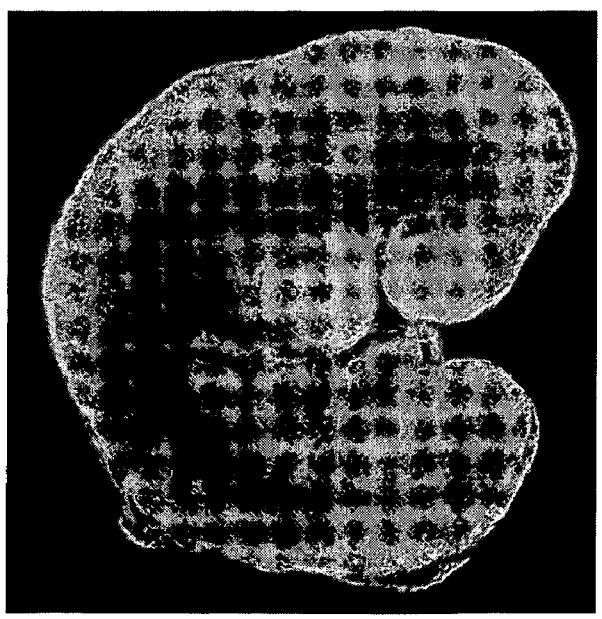

EMBRYONIC STEM CELL SELF MAINTENANCE AND RENEWAL REPORTER

This Application claims priority to provisional patent application Ser. No. 60/644,785, filed Jan. 18, 2005, which is herein incorporated by reference in its entirety.

This invention was funded in part by Grant Nos. R 37 Dk 042989 and U01 DK633481 awarded by the NIH. The government may have certain rights in the invention.

FIELD OF THE INVENTION

The present invention relates to methods and compositions for assaying embryonic stem cell maintenance. In particular, the present invention provides reporter constructs for stem cell pluripotency and differentiation and cells and organisms containing such constructs.

BACKGROUND OF THE INVENTION

Recent published reports on the isolation and successful culturing of the first human pluripotent stem cell lines have generated great excitement and have brought biomedical research to the edge of a new frontier (National Institutes of Health, Office of the Director, "Stem Cells: A Primer"). Stem cells have the ability to divide for indefinite periods in culture and to give rise to specialized cells. They are best described in the context of normal human development. Human development begins when a sperm fertilizes an egg and creates a single cell that has the potential to form an entire organism. This fertilized egg is totipotent, meaning that its potential is total. In the first hours after fertilization, this cell divides into identical totipotent cells. This means that either one of these cells, if placed into a woman's uterus, has the potential to develop into a fetus. In fact, identical twins develop when two totipotent cells separate and develop into two individual, genetically identical human beings. Approximately four days after fertilization and after several cycles of cell division, these totipotent cells begin to specialize, forming a hollow sphere of cells, called a blastocyst. The blastocyst has an outer layer of cells and inside the hollow sphere, there is a cluster of cells called the inner cell mass.

The outer layer of cells will go on to form the placenta and other supporting tissues needed for fetal development in the uterus. The inner cell mass cells will go on to form virtually all of the tissues of the human body. Although the inner cell mass cells can form virtually every type of cell found in the human body, they cannot form an organism because they are unable to give rise to the placenta and supporting tissues necessary for development in the human uterus. These inner cell mass cells are pluripotent—they can give rise to many types of cells but not all types of cells necessary for fetal development. Because their potential is not total, they are not totipotent and they are not embryos. In fact, if an inner cell mass cell were placed into a woman's uterus, it would not develop into a fetus.

The pluripotent stem cells undergo further specialization into stem cells that are committed to give rise to cells that have a particular function. Examples of this include blood stem cells, which give rise to red blood cells, white blood cells and platelets; and skin stem cells that give rise to the various types of skin cells. These more specialized stem cells are called multipotent.

While stem cells are extraordinarily important in early human development, multipotent stem cells are also found in children and adults. For example, consider one of the best understood stem cells, the blood stem cell. Blood stem cells reside in the bone marrow of every child and adult, and in fact, they can be found in very small numbers circulating in the blood stream. Blood stem cells perform the critical role of continually replenishing our supply of blood cells—red blood cells, white blood cells, and platelets—throughout life. A person cannot survive without blood stem cells.

Multipotent stem cells have not been found for all types of adult tissue, but discoveries in this area of research are increasing. For example, until recently, it was thought that stem cells were not present in the adult nervous system, but, in recent years, neural stem cells have been isolated from the rat and mouse nervous systems. The experience in humans is more limited. In humans, neural stem cells have been isolated from fetal tissue and a kind of cell that may be a neural stem cell has been isolated from adult brain tissue that was surgically removed for the treatment of epilepsy. In animals, it has been shown that some adult stem cells previously thought to be committed to the development of one line of specialized cells are able to develop into other types of specialized cells. For example, recent experiments in mice suggest that when neural stem cells were placed into the bone marrow, they appeared to produce a variety of blood cell types. In addition, studies with rats have indicated that stem cells found in the bone marrow were able to produce liver cells. These exciting findings suggest that even after a stem cell has begun to specialize, the stem cell may, under certain conditions, be more flexible than first thought.

Research on human adult stem cells suggests that these multipotent cells have great potential for use in both research and in the development of cell therapies. For example, there would be many advantages to using adult stem cells for transplantation. If one can isolate the adult stem cells from a patient, coax them to divide and direct their specialization and then transplant them back into the patient, it is unlikely that such cells would be rejected by the patient's immune system. The use of adult stem cells for such cell therapies could reduce the practice of using stem cells that were derived from human embryos or human fetal tissue, sources that trouble many people on ethical grounds.

Stem cells can be made to differentiate under certain culture conditions. However, in some applications it is desirable to maintain stem cells in a non-differentiated state. Additional methods for assaying the differentiation status of stem cells are needed.

SUMMARY OF THE INVENTION

The present invention relates to methods and compositions for assaying embryonic stem cell maintenance. In particular, the present invention provides reporter constructs for stem cell pluripotency and differentiation and cells and organisms containing such constructs.

Accordingly, in some embodiments, the present invention provides reporter constructs that exhibit altered reporter gene expression in differentiated cells or organisms verses stem cells. The present invention further provides methods of using the cells and organisms in research and drug screening applications.

For example, in some embodiments, the present invention provides a composition comprising at least a portion of a bacterial artificial chromosome (BAC) or other vector, wherein the BAC comprises nanog gene regulatory elements (e.g., nanog gene A box and B box elements) operably linked to a reporter gene. In some embodiments, the reporter gene encodes a fluorescent protein (e.g., green or red fluorescent protein) or other detectable moiety. In some embodiments, the BAC further comprises a selectable marker.

The present invention further provides an embryonic stem cell (e.g., a mouse or a human embryonic stem cell) comprising the BAC. In other embodiments, the present invention provides an embryonic germ cell comprising the BAC. In yet other embodiments, the present invention provides a primordial germ cell comprising the BAC. In still further embodiments, the present invention provides a transgenic non-human animal comprising the BAC. In some embodiments, the animal is a rodent (e.g., a mouse or a rat).

The present invention additionally provides a method, comprising contacting an embryonic stem cell comprising at least a portion of a bacterial artificial chromosome (BAC), wherein the BAC comprises nanog gene regulatory elements operably linked to a reporter gene with a test compound; and observing the level of reporter gene expression in the presence of the test compound relative to the level in the absence of the test compound. In some embodiments, the reporter gene encodes a fluorescent protein (e.g., green or red fluorescent protein). In some embodiments, the BAC further comprises a selectable marker. In some embodiments, the test compound induces differentiation of the embryonic stem cell. In other embodiments, the test compound prevents differentiation of the stem cell. In some preferred embodiments, the level of reporter gene expression decreases upon differentiation of the embryonic stem cell.

The present invention also provides a method, comprising altering the level of expression of one or more genes in an embryonic stem cell comprising at least a portion of a bacterial artificial chromosome (BAC), wherein the BAC comprises nanog gene regulatory elements operably linked to a reporter gene with a test compound; and observing the level of reporter gene expression following the altering the level of expression of one or more genes relative to the level prior to the altering the level of expression of one or more genes. In some embodiments, the level of expression of the one or more genes is decreased. In other embodiments, the level of expression of the one or more genes is increased.

Other embodiments of the invention are described in the description and examples below.

DESCRIPTION OF THE FIGURES

FIG. 1 (SEQ ID NO:55) provides sequence information for A-box, HygEGFP, SV40 polyA and B-box. Underlined: AscI, XmaI, NotI, PacI and FseI sites, lowercase: intronic sequences. UPPERCASE italic: Nanog exon sequences. Double underline: sequence encoding Hygromycin-resistance. bold: start and stop codons, respectively. The symbol ( . . . ) represents sequence encoding EGFP. The symbol ( - - - ) represents SV40polyA sequences.

FIG. 3B shows a schematic of BAC cloning.

FIG. 9 shows that NeFREC(g)-SF downregulate Nanog/GFP in response to the removal of LIF and Bmp4. A, FACS analysis of NeFREC(g)-SF (green, 94.8%) upon removal of LIF and Bmp4 for 2 days (red, 33.5%). B, FACS analysis of NeFREC(g)-SF (green, 94.8%) upon removal of LIF only for 2 days (blue, 70.9%) and 3 days (red, 47.3%). CCE ES cells were used as negative staining control (black).

DEFINITIONS

Figure 2:
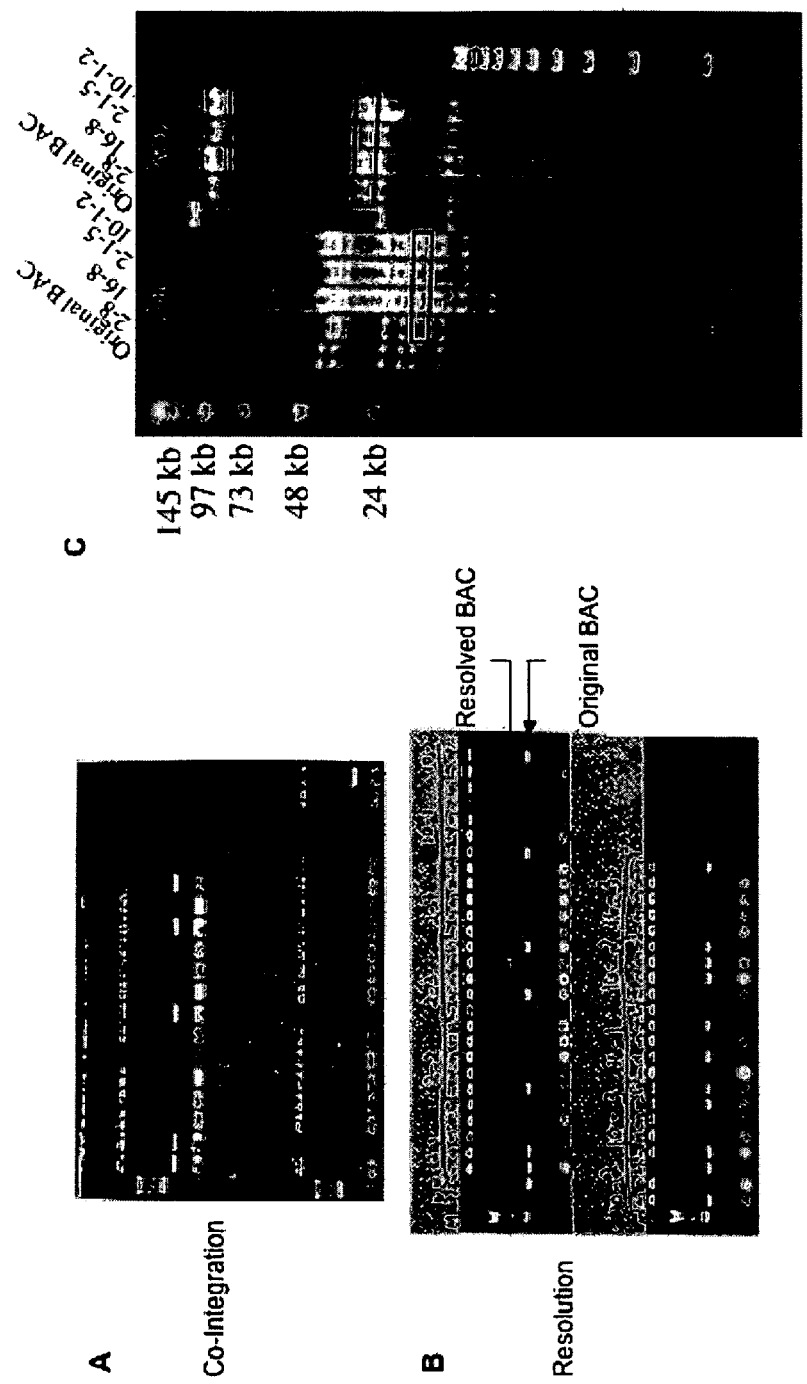
FIG. 2 shows the results of BAC recombineering. A, PCR-confirmation of co-integration through A- or B-box. B, Confirmation of resolution by PCR. C, Pulse-field gel electrophoreses of PacI or PvuI digested BAC RP23-180N22 (Original BAC) and 4 modified Nanog/GFP BACs (#2-8, 16-8, 2-1-5 and 10-1-2).

To facilitate an understanding of the present invention, a number of terms and phrases are defined below:

As used herein, the term "reporter gene" refers to a gene encoding a protein or other molecule that may be assayed. Examples of reporter genes include, but are not limited to, luciferase (See, e.g., deWet et al., Mol. Cell. Biol. 7:725 [1987] and U.S. Pat Nos., incorporated herein by reference), green fluorescent protein (See, e.g., U.S. Pat. Nos., incorporated herein by reference), chloramphenicol acetyltransferase, β-galactosidase, alkaline phosphatase, LacZ, hCD4 or hIL2 receptor, and horse radish peroxidase.

As used herein, the term "stem cell" or "undifferentiated cell" refers to self-renewing multipotent cells that are capable of giving rise to more stem cells, as well as to various types of terminally differentiated cells.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')₂ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')₂ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "mimetic" refers to a small molecule compound that mimics the binding of a ligand to its receptor or binding partner.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression"-0 refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA or RNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA or RNA into a cell where the foreign DNA or RNA fails to integrate into the genome of the transfected cell. The foreign DNA or RNA persists in the nucleus or cytoplasm of the transfected cell for several days. During this time the foreign DNA or RNA is subject to the regulatory controls that govern the expression of endogenous genes in the chromosomes. The term "transient transfectant" refers to cells that have taken up foreign DNA or RNA but have failed to integrate this DNA or RNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp.16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reactions that occur within a natural environment.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "drug" refers to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered.

DETAILED DESCRIPTION OF THE INVENTION

The present invention relates to methods and compositions for assaying embryonic stem cell maintenance. In particular, the present invention provides reporter constructs for stem cell pluripotency and differentiation and cells and organisms containing such constructs.

ES cells provide a model system to investigate early development and complex diseases, and an assay system for drug discovery and development and toxicology tests, as well as a source for future cell replacement therapies (Keller, 2005. Genes Dev. 19:1129-1155). A unique property of ES cells is their extensive in vitro self-renewal capacity. ES can differentiate into all three germ layers as well as germ cells in vitro and in vivo (Loebel et al., Dev Biol. 264:1-14; Keller, 2005, supra). In order to achieve this, ES cells, like all stem cells, must be able to properly balance self-renewal versus differentiation as well as regulate proliferation and cell death processes. If the growth and differentiation of ES cells can be controlled, then any somatic and germ cell type or tissue can be produced at will. Clearly, there is a need to gain a firm understanding of how cell fate decisions are regulated in these cells before this goal can be achieved and the promise of ES cells be realized.

Knowledge of the growth factors and machinery regulating ES cell self-renewal and differentiation is detailed for some pathways and sparse for others (Rao, 2004. Dev Bio. 275: 269-286). The recently identified homeobox transcription factor Nanog is one of the components required for proper ES cell maintenance (Mitsui et al., 2003 Cell 113: 631-642; Chambers et al., 2003 Cell 113: 643-655; Hatano et al., 2005 Mech. Dev. 122:67-79). Nanog is also observed as a transcript in germ cells (Yamaguchi et al., Gene Expression Patterns 5:639-646). Experiments conducted during the course of development of the present invention (See e.g. Experimental section below) resulted in the development of reporter constructs and cell lines for stem cell differentiation that utilize Nanog regulatory elements linked to a reporter gene. The reporter constructs and cell lines of the present invention find use in research and drug screening applications. Exemplary, non-limiting applications of the present invention are described below.

I. Reporter Constructs

In some embodiments, the present invention provides reporter constructs for assaying stem cell pluripotency and differentiation. In certain exemplary embodiments, the reporter constructs have the following features. In some embodiments, the reporter constructs are based on bacterial artificial chromosomes (BACs) and comprise at least a portion of a BAC. In preferred embodiments, the constructs comprise nanog gene regulatory elements (e.g., Nanog A and B box elements) linked to a reporter construct (e.g., green or red fluorescent protein). In some embodiments, reporter constructs further comprise a selectable marker (e.g., derived from the BAC backbone or inserted during construction of the construct). Exemplary reporter constructs of the present invention are described in FIG. 1 and the illustrative examples below.

The present invention is not limited to BAC vectors. Other suitable vector backbones are known to those skilled in the art and may be utilized in the methods of the present invention. Examples include, but are not limited to, chromosomal, non-chromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies).

In some embodiments, reporter constructs of the present invention are used to generate embryonic stem cells that stably express the reporter constructs. The present invention is not limited to embryonic stem cells from a particular animal. Indeed, the methods of the present invention are suitable for the generation of reporter ES, embryonic germ and primordial germ cell derived from any animal including, but not limited to, mouse and human. In preferred embodiments of the present invention, the reporter constructs of the present invention exhibit reporter gene activity (e.g., fluorescence) that is lost upon differentiation. The cells thus serve as reporters for stem cell maintenance and differentiation (See illustrative examples below).

II. Uses of Reporter Constructs and Cell Lines

The reporter constructs and cell lines of the present invention find use in a variety of research and drug screening applications. Exemplary non limiting examples of uses of the cell lines and constructs of the present invention are described in greater detail below.

A. Drug Screening

In some embodiments, embryonic stem cell lines comprising nanog reporter constructs of the present invention find use in drug screening applications. For example, in some embodiments, the cell lines are used to screen for small molecules involved in ESC self-renewal and maintenance or in inducing ESC differentiation. Test compounds are contacted with the cell lines and differentiation or lack of differentiation in response to the test compounds is assayed by reporter signal.

In other embodiments, drug screening assays are performed in primordial germ cells (PGCs) and embryonic germ (EG) cells comprising the reporter constructs of the present invention. In some embodiments, small molecule test compounds are screened for their ability to regulate development, differentiation, and nuclear reprogramming.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

B. Research Applications

The present invention is not limited to drug screening applications. The reporter cell lines of the present invention further find use in research applications. For example, in some embodiments, expression of genes thought to be involved in differentiation or nuclear reprogramming are up or down regulated and the effect on differentiation is assayed. For example, in some embodiments, genes suspected of being involved in differentiation or nuclear reprogramming are knocked out in ES, EG, PGC or somatic cells of the present invention comprising Nanog reporter constructs and the effect on differentiation is assayed. Gene expression may be reduced using any suitable method including, but not limited to RNAi, antisense, or recombination.

In other embodiments, gain of function assays where exogenous genes are upregulated (e.g., via insertion of a construct expressing the gene of interest) are assayed for their effect on differentiation of the cells of the present invention. In some embodiments, genomic libraries are utilized to screen the upregulation of large number of genes.

In other embodiments, research applications involved the identification of Nanog transcriptional regulators (e.g. using the drug screening methods described above). In still further embodiments, research applications include monitoring and studying early embryonic development (e.g., through the use of embryos or EG cell comprising the reporter constructs of the present invention). In some embodiments, the effects of genes and small molecules on early embryonic development and other aspects of reproduction are studied using the cells and constructs of the present invention.

In yet other embodiments, the present invention provides methods of isolating cell populations (e.g., from cell cultures or non-human animals) based on their levels of reporter gene expression from the constructs of the present invention. As described in the experimental section below (See e.g., Example 8), it is possible to isolate cells from a mixed population based on their level of expression from a Nanog/GFP reporter construct. Such cells find use in the research and drug screening applications of the present invention.

C. Transgenic Animals

In some embodiments, the present invention provides transgenic animals comprising the reporter constructs of the present invention (See e.g., Experimental section below). Such transgenic animals find use in research and therapeutic applications. For example, in some embodiments, the transgenic animals find use in the study of embryogenesis, differentiation, reproduction and fertility. The transgenic animals further find use in drug screening applications for drugs that regulate differentiation, embryogenesis, reproduction and fertility.

In other embodiments, the present invention provides cells established from such transgenic mice (e.g., embryonic fibroblast cell lines). In some embodiments, cell lines are established based on expression from a Nanog reporter construct of the present invention. Such cell lines find use in the research and drug screening applications of the present invention.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., truncation mutants). Methods for homologous recombination are described in U.S. Pat. No. 5,614,396, incorporated herein by reference.

D. Antibodies

In some embodiments, the present invention provides methods for generating antibodies against proteins of interest (e.g., cell surface molecules on cells identified using the selection methods of the present invention). In some embodiments, cells isolated from cell lines or transgenic animals based on expression from nanog reporter constructs are utilized for the generation of monoclonal or polyclonal antibodies (e.g., against cell surface proteins or other proteins of interest in the cells).

Various procedures known in the art may be used for the production of polyclonal antibodies directed against a protein of interest. For the production of antibody, various host animals can be immunized by injection with the peptide corresponding to the epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for the protein of interest. In some embodiments, humanized antibodies are generated (See e.g., U.S. Pat. Nos. 6,180,370, 5,585,089, 6,054,297, and 5,565,332; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay).

The foregoing antibodies can be used in methods known in the art relating to the localization and structure of proteins of interest (e.g., for Western blotting), measuring levels thereof in appropriate biological samples, etc. The antibodies can be used to detect the protein of interest in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of the protein of interest using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of the protein of interest detected by immunoblotting (Western blotting). Immunoblotting techniques are generally more effective with antibodies generated against a peptide corresponding to an epitope of a protein, and hence, are particularly suited to the present invention.

EXPERIMENTAL

The following examples are provided in order to demonstrate and further illustrate certain preferred embodiments and aspects of the present invention and are not to be construed as limiting the scope thereof.

Example 1

Materials and Methods

ES cell growth and differentiation. ES cells were maintained on gelatin-coated tissue culture plates in Dulbecco's Modified Eagels Medium (DMEM; Invitrogen/Gibco) supplemented with 15% fetal calf serum (FCS), 1 mM sodium pyruvate, 2 mM L-glutamine (Invitrogen/Gibco), 0.1 mM non-essential amino acids (Invitrogen/Gibco), 100 U/ml penicillin, 100 µg/ml streptomycin, $1\times10^{-4}$ M 2-Mercaptoethanol (2-ME) and 1000 U/ml leukemia inhibitory factor (LIF; ESGROW, Chemicon), henceforth referred to as ES medium. Medium was changed every day and cells were split every second day.

Alternatively, ES cells were maintained on gelatin-coated tissue culture plates in a 1:1 mixture of Neurobasal with N2-supplement (Invitrogen/Gibco) and DMEM/F12 with B27 (Invitrogen/Gibco) supplemented with 10% fraction V bovine serum albumin (BSA; Sigma) and 100 U/ml penicillin, 100 µg/ml streptomycin, $1\times10^{-4}$ M 2-ME), 1000 U/ml LIF and 10 ng/ml bone morphogenic protein (Bmp) 4 (R&D Systems), henceforth referred to as SF-ES medium. Medium was changed every day and cells split every second day.

One day prior to differentiation cells were plated on gelatinized culture dishes in the aforementioned medium. Differentiation was induced either by removal of LIF or removal of LIF and addition of retinoic acid (RA, Sigma) if grown in ES medium or either LIF or Bmp4 or both if grown in SF-ES medium.

For the generation of embryoid bodies (EBs), ES cells were trypsinized and plated at 500000 cells in bacterial Petri dishes in 10 ml Iscove's Modified Dulbecco's Medium (IMDM, Invitrogen/Gibco) supplemented with 15% FCS, 2 mM L-glutamine, 200 µg/ml apo-transferrin (Sigma), 50 µg/ml L-ascorbic acid (Sigma), 100 U/ml penicillin, 100 µg/ml streptomycin, 4.5 mM Monothioglycerole, referred to hereforth as EB medium. Half the medium was changed every other day.

Cultures were maintained in a humidified chamber in 5% $CO_2$/air mixture at 37° C.

Alkaline phosphatase staining. Staining was performed using an alkaline phosphatase staining kit (Sigma) according to the manufacturer's instruction.

Microscopy. Microscopy was performed on a Nikon Eclipse TE2000-U microscope with appropriate filter sets, CoolSnapES (black and white/fluorescence) and DXM1200F (color) cameras, and MetaView (black and white/fluorescence) and ACT (color) image-processing software.

Cell surface staining, FACS analysis and Cell Sorting. Standard conditions were used to stain the cells. Cell suspensions were analyzed on a FACS Sort (Becton Dickinson). Cell sorting was performed using a FacsVantage with DiVa Software (Becton Dickinson).

Gene Expression Analysis. For gene specific PCR, total RNA was extracted using Trizol (Invitrogen) as directed by the manufacturer. Pelleted total RNA was DNAse I (Invitrogen) treated to remove remnant DNA according to the manufacturer's instruction, phenol/chloroform/isopropanol extracted and precipitated overnight at −80° C. DNA-free total RNA was washed with 80% ethanol, dried at room temperature and resuspended in DEPC-treated water. cDNA synthesis was performed with maximally 5 µg of RNA using random primers (Invitrogen) and Superscript II reverse transcriptase (Invitrogen) as directed by the manufacturer. The PCR-reactions were performed with 0.25 µM of each primer, 0.2 µM of each dNTP, 0.5 U Taq DNA polymerase and supplemented PCR-buffer (Hoffmann-LaRoche). Amplified products were separated on agarose gels and visualized using a GelDoc System (BioRad).

RNA shRNA Transfection. For transfection of RNA shRNA, cells were harvested, washed with DMEM and resuspended at $2\times10^5$/ml in medium without penicillin and streptomycin. 250 µl of medium without penicillin and streptomycin was added per gelatin pre-coated well of a 24-well culture plate. In order to prepare the RNA shRNA transfection mixture per well, 10-20 µl of RNA shRNA [1 pmole/µl] was mixed with OptiMEM (Invitrogen/Gibco) in a final volume of 50 µl. In a separate tube, 1 µl Lipofectamine2000 (Invitrogen) was added to 49 µl of OptiMEM per sample. The RNA shRNA/OptiMEM and Lipofectamine/OptiMEM solutions were combined, mixed, incubated for 20 min at room temperature and added to the well. Then, 250 µl of cell solution, i.e., $5\times10^4$ cells/well, were added and the 24-well plate incubated in a humidified chamber in 5% $CO_2$/air mixture at 37° C. Twenty-four hours after transfection, medium was replaced with appropriate medium with penicillin and streptomycin.

Southern Blot Analysis. Genomic DNA was prepared according to standard protocols. DNA was digested and separated on agarose gels and transferred to Hybond-N+membranes (GE Healthcare) by alkaline blotting. Radioactive probes of a 3.8 kb EcoRI fragment from the H19 locus were made using Ready-To-Go Labelling (GE Healthcare). Blots were hybridized with the $^{32}$P-labelled probe at 42° C. overnight following prehybridization. Membranes were washed twice in 2×SSC/0.1% SDS at 65° C. for 30 min and twice in 0.1×SSC/0.1% SDS at 65° C. for 30 min. Membranes were placed into a PhosphoImager cassette and analyzed after 20-24 hr exposure.

Example 2

Generation of Nanog Enhanced Fluorescent Reporter ES Cells (NeFREC(g))

In order to distinguish undifferentiated from differentiated ES cells as well as to track germ cells or their precursors and to isolate cells representing these populations, ES cells were generated that express fluorescent reporters under the control of Nanog regulatory elements.

Generation of Nanog/enhanced Fluorescent Reporter DNA by BAC recombineering and subcloning. A Bacterial Artificial Chromosome (BAC) RP23-180N22 (Invitrogen/ResGen; sequence accession number AC131715) carrying the mouse Nanog locus was selected from the mouse ENSEMBL Internet site.

A Hygromycin-resistance enhanced green fluorescent protein gene fusion (henceforth referred to as HygEGFP) sequence followed by the SV40 polyadenylation (polyA) sequence (Clontech) was recombined into BAC RP23-180N22 to create Nanog/GFP BAC. In brief, the original shuttle vector was modified by replacing the XmaI/NotI EGFP fragment with a XmaI/NotI HygEGFP fragment. Oligos 5'-AAACCCGGGGCCGCCACCATGAAAAAGC-CTGAAC-3' (SEQ ID NO:1) and 5'-CTCGCGGCCGCTT-TACTTGTACACG-3' (SEQ ID NO:2) were used to create the 5'XmaI and the 3' NotI restriction sites by PCR using pHygEGFP (Clontech) as a template.

Figure 3:
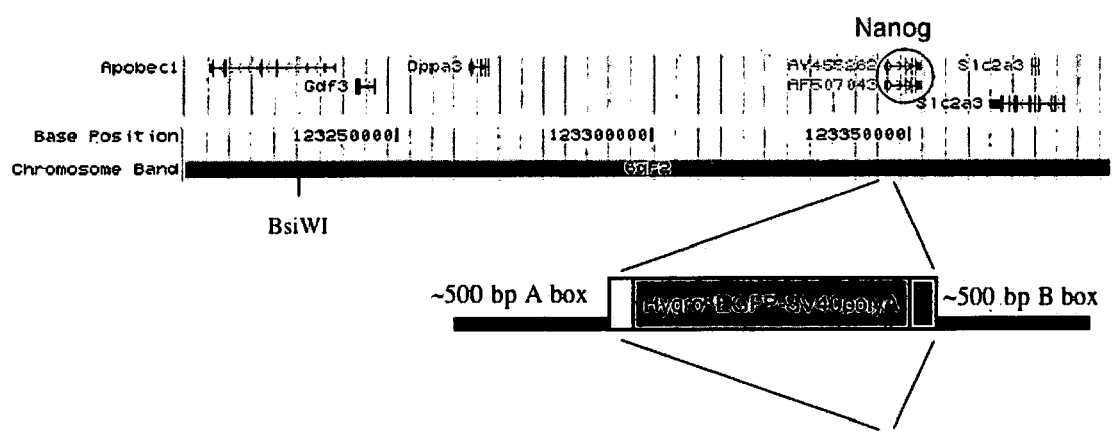
FIG. 3 shows a schematic view of Nanog/GFP BAC. A. Upper graph depicts the genomic view of BAC RP23-180N22 on mouse chromosome 6. Genes are indicated by name. Exons are represented by bars and arrows indicate 5'-to-3' orientation of the transcripts. HygEGFP-SV40 polyA (gene) is replacing coding sequences in the first exon of Nanog. The left box represents the 5' untranslated region of Nanog while the right box represents the 3' translated region of exon 1 of Nanog.
Figure 3:
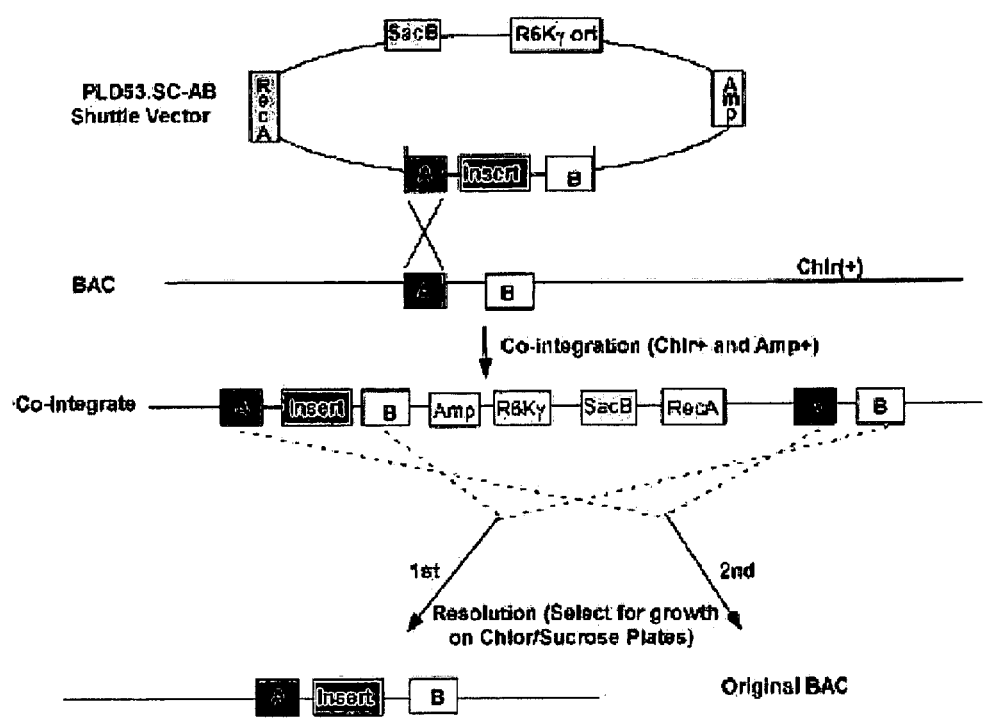

The Nanog locus 5' (A-box) and 3' (B-box) homologous regions were PCR-amplified using primers 5'-CCCG-GCGCGCCCCAATGTGAAGAGCAAGCAA-3' (SEQ ID NO:3) and 5'-AGTCCCGGGCAGCCTTCCCACAGAAA-GAG-3' (SEQ ID NO:4) and 5'-GCGTTAATTAAGAG-GAAGCATCGAATTCTGG-3'(SEQ ID NO:5) and 5'-ACTGGCCGGCCGTTTGGAAGGAGCACTGAGC-3' (SEQ ID NO:6), respectively. The PCR fragments were cloned into the AscI/XmaI and the PacI/FseI sites of the modified shuttle vector. FIG. 1 contains the sequence information of the A-box, HygEGFP, SV40 polyA and B-box. BAC modification was performed according to standard protocol (Sparwasser et al., 2004 Genesis 38:39-50). Oligos 5'-TGAACTTGTGGCCGTTTACG-3' (SEQ ID NO:7) and 5'-TGAACTTGTGGCCGTTTACG-3' (SEQ ID NO:8) were used to check for co-integration in the A-box and oligos 5'-TGCCCGACAACCACTACCTG-3' (SEQ ID NO:9) and 5'-TTCAGACCTTGGCTCCAGAT-3' (SEQ ID NO:10) for the B-Box (FIG. 2A). Resolved clones were identified by PCR using primers 5'-TGAACTTGTGGCCGTTTACG-3' (SEQ ID NO:11) and 5'-TTCAGACCTTGGCTCCAGAT-3' (SEQ ID NO:12) (FIG. 2B). Nanog/GFP BAC DNA was isolated using Nucleobond BAC Maxi Kit (BD Biosciences). To determine whether any unexpected deletions or recombinations were generated during the modification process, high resolution fingerprinting of the original or modified BAC was carried out after PacI or PvuI digestion (FIG. 2C). FIG. 3 shows a schematic of the modified BAC.

In order to create the 6033 bp 5' fragment, HygroEGFP-SV40polyA and 4785 bp downstream fragment cassette, Nanog/GFP BAC RP23-180N22 was digested with SpeI and BstBI, separated on a 0.7% agarose gel, and a 12.8 kb fragment isolated and subcloned into the SpeI/ClaI site pBSK (Stratagene) resulting in plasmid 346. In order to create a red fluorescent reporter, the 12.8 kb SpeI/XhoI fragment from plasmid 346 was cloned into SpeI and XhoI digested pBSK deleted of its NotI site (346ΔNotI), followed by replacing the 1764 bp HygroEGFP with a 705 bp XmaI/NotI DsRedExpress (Clontech) fragment resulting in plasmid 346R. In plasmid 346d2R, the DsRedExpress fragment of plasmid 346R was replaced by a 830 bp XmaI/NotI fragment of a destabilized version of DsRedExpress (Clontech).

Figure 4C:
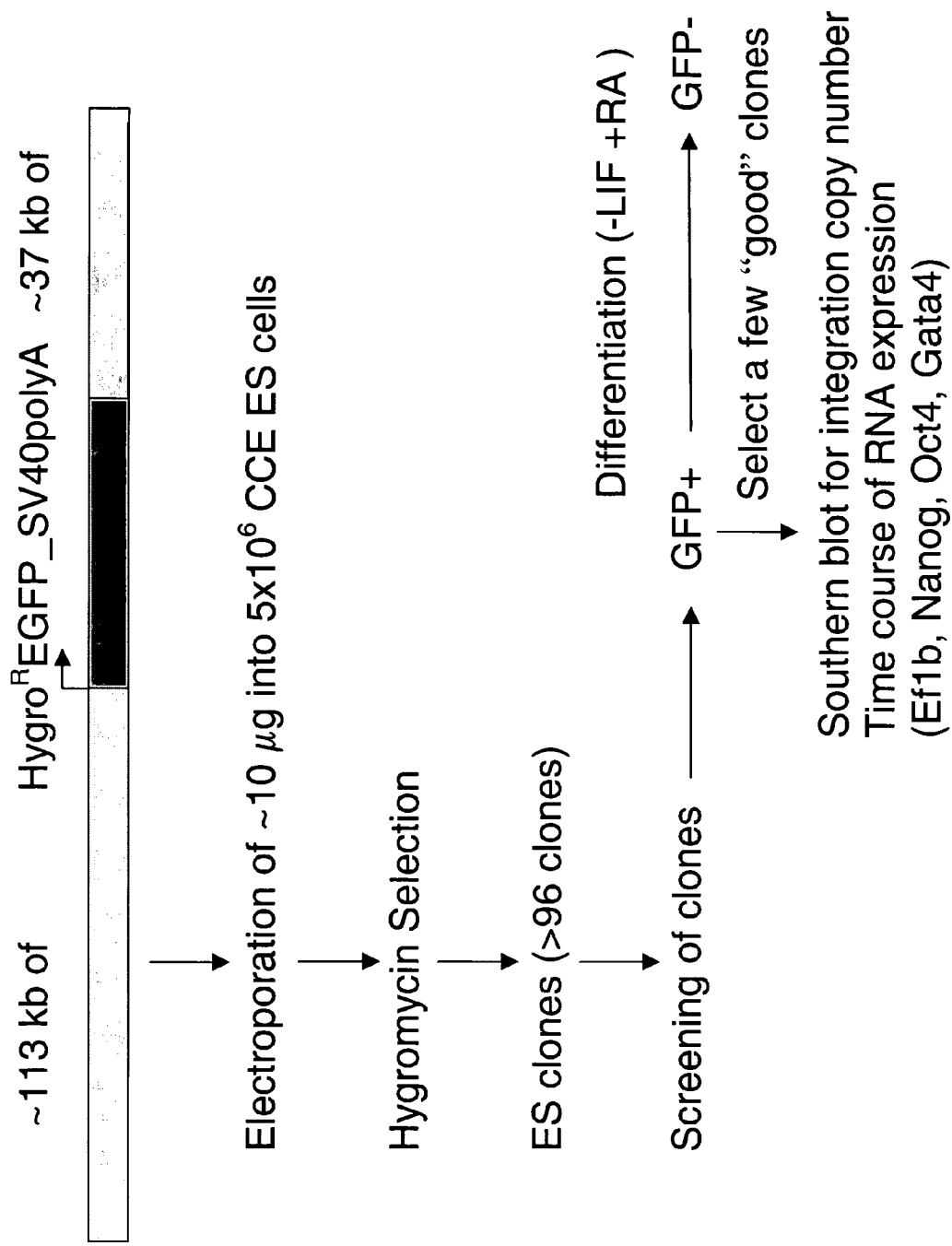
FIG. 4 shows green Fluorescence of an established NeFREC(g) clone. A, brightfield, fluorescence and overlay of bright field and fluorescence microscopy pictures of a growing NeFREC(g) colony. B, Flow cytometry of a NeFREC(g) clone. Black: wild-type CCE ES cells. C, Generation of Nanog_HygroREGFP_SV40polyA BAC Transgenic ES Cell.

NeFREC(g). In order to establish the Nanog enhanced Green Fluorescent Reporter ES Cells [NeFREC(g)], BsiWI digested Nanog/GFP BAC DNA was electroporated into $5 \times 10^6$ CCE ES cells using a BioRad Gene Pulser (BioRad) set to 0.24 kV, 200 Ohms and 500 uFD. Electroporated ES cells were plated onto gelatin-coated 10-cm dishes in 10 ml ES cell growth medium. Since Nanog is required for ES cell identity, and the DNA engineered to express HygEGFP from Nanog-regulatory elements, transgenic ES cells were selected in ES medium supplemented with 250 μg/ml Hygromycin (Invitrogen) from day 2 onwards. Ten to 14 days after selection individual GFP+ colonies were picked and expanded in selection medium (FIG. 4).

Figure 5:
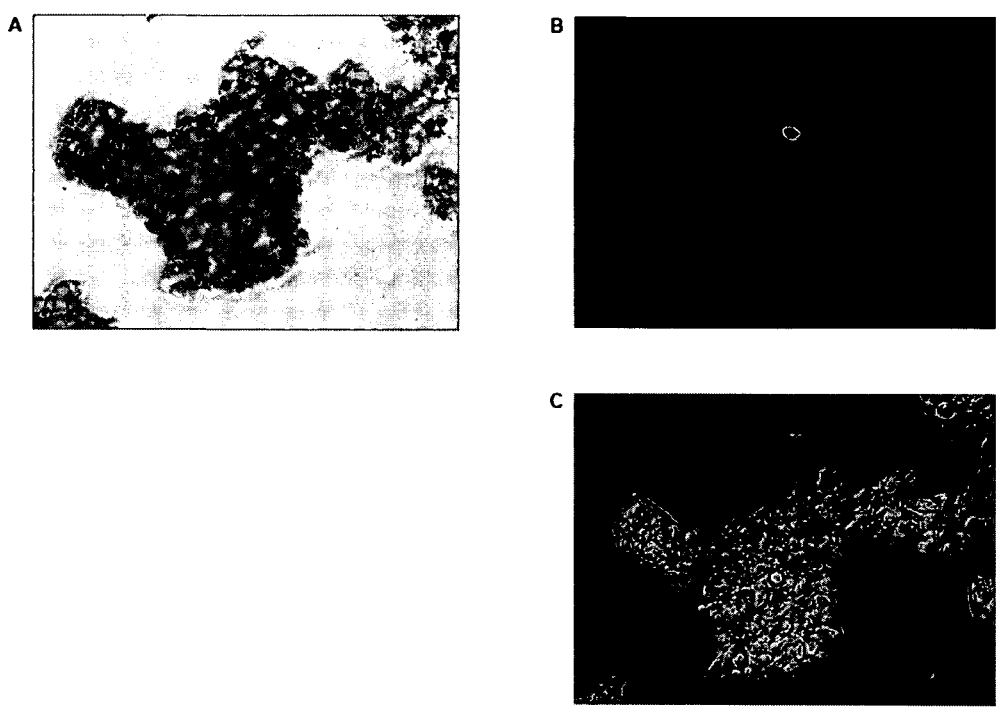
FIG. 5 shows that NeFREC(g) express alkaline phosphatase. A, An established NeFREC(g) clone expresses alkaline phosphatase, a marker for undifferentiated ES cells. B, The same colony as shown in A is also positive for Nanog/GFP. C, Overlay of brightfield and fluorescence microscopy pictures of the same colony as in A and B.

Undifferentiated ES cells are defined by the expression of alkaline phophatase (Bernstine et al., 1973. PNAS 70:3899-3903). Undifferentiated NeFREC(g) express GFP and are positive for alkaline phosphatese (FIG. 5).

NeFREC(g)-SF. An established and characterized NeFREC(g) line was adapted to serum-free growth in SF-ES medium according to standard protocol and is designated NeFREC(g)-SF.

NeFREC(r) and NeFREC(d2r). NeFREC(r) and (d2r) were established by co-transfecting SpeI/XhoI digested 346R or 346d2R plasmid DNA, respectively, together with DNA conferring Hygromycin resistance at a 10:1 ratio using Lipofectamine 2000 (Invitrogen) according to the manufacturers instructions. Colony selection, expansion and freezing is as described for NeFREC(g).

Established cell lines were frozen in 65% ES medium, 25% FCS, and 10% DMSO (Sigma) and stored in liquid nitrogen.

A fluorescent marker for Nanog expression and, hence, ES self-renewal and maintenance, enables analysis of life cells by microscopy or flow cytometry. NeFRECs are easy to handle, and a convenient and quick tool, which greatly facilitate genetic and chemical genomics screens to evaluate their roles in ES cell maintenance and differentiation (see Examples 3 and 5-7).

Example 3

Differentiation of NeFRECs in Response to Retinoic Acid

Retinoic acid (RA) is widely used to induce rapid ES cell differentiation (Tighe et al., 2004. J. Cell. Physiol. 198(2): 223-229). Differentiated ES cells turn off expression of the ES cell-specific genes Pou5f1 (Pesce et al. 1998. BioEssays 20:722-732), Sox2 (Avilion et al., 2003. Genes Dev. 17:126-140), Nanog (Mitsui et al., 2003. Cell 113:631-642; Chambers et al., 2003. Cell 113 643-655; Hatano et al., 2005. Mech. Dev. 122:67-79) and induce expression of lineage marker genes such as Gata4 (Arceci et al., 1993 Mol. Cell. Biol. 13:2235-2246).

Figure 6:
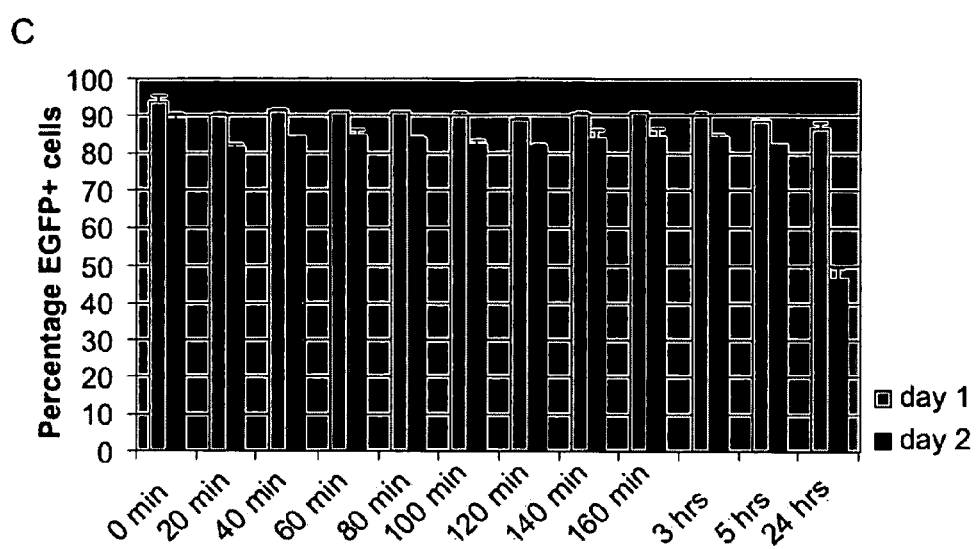
FIG. 6 shows that NeFREC(g) differentiate and downregulate Nanog/GFP in response to retinoic acid. A. FACS analysis of Nanog/GFP levels in 4 NeFREC(g) clones and wild-type CCE ES cells upon RA-induced differentiation (upper panel). B. RA-induced downregulation in Nanog/GFP in two NeFREC(g) clones is concentration dependent. C. RA-pulse experiment with NefREC(g).

NeFREC(g) clones. To determine the dynamics of Nanog/GFP expression of NeFREC(g) clones in response to RA, 4 individual clones (numbers 4, 9, 20 and 23) were analyzed in detail (FIG. 6a upper panel). $2.5 \times 10^4$ cells were plated in 0.5 ml ES medium the day before RA treatment. ES medium without LIF and supplemented with 10 μM RA (10 mM stock dissolved in 100% ethanol) was added to cells 24 hours post-plating (indicated as day 0). Nanog/GFP levels in treated cells were measured daily, day 0 to day 3, by flow cytometry. FACS analysis showed that Nanog/GFP expression is substantially downregulated within one day of RA treatment. By day 3, less than 5% cells remain Nanog/GFP+ in response to RA treatment. RT-PCR analysis showed that endogenous Nanog mRNA expression (5'-AGGCTTTGGAGACAGTGAG-GTGC-3' (SEQ ID NO:13) and 5'-TACCCTCAAACTC-CTGGTCCTTC-3' (SEQ ID NO:14)) correlates well with Nanog/GFP levels (FIG. 6A lower panel). In contrast to downregulation of Nanog/GFP levels and Nanog mRNA expression, Gata4 (5'-GCCTGTATGTAATGCCTGCG-3' (SEQ ID NO:15) and 5'-CCGAGCAGGAATTTGAA-GAGG-3' (SEQ ID NO:16)), a marker gene of early endoderm development, is upregulated upon RA treatment and indicates ES cell differentiation (Arceci et al., 1993 Mol. Cell. Biol. 13:2235-2246). Eef1b gene expression was used as loading control (5'-TTACCTGGCGGACAAGAGCT-3' (SEQ ID NO:17) and 5'-CCAATTTAGAGGAGCCCCACA-3' (SEQ ID NO:18)).

To further determine the dynamics of Nanog/GFP expression of NeFREC(g), a RA dosage response experiment, ranging from 0.2 to 10 μM RA, was performed (FIG. 6B). An RA dosage of 0.2 μM is sufficient to induces a rapid and significant downregulation of Nanog/GFP expression in NeFREC(g). Omitting LIF from the ES medium also induces loss of Nanog/GFP expression in these cells at a slower rate compared to RA treatment. Forty percent of the cells still remain Nanog/GFP+ by day 3. A RA pulse experiment was performed to determine the time required to initiate Nanog/GFP downregulation (i.e. differentiation) in response to 1 μM of RA (FIG. 6C). $2.5 \times 10^4$ cells were plated initially in 0.5 ml media per well in a 24-well plate the day before treatment. Cells were pulsed with 1 μM RA in ES medium without LIF for the indicated time periods and then changed to fresh ES medium. Nanog/GFP expression was measured after one day and two days of RA treatment. The results show that a 24-hour treatment with 1 μM RA is sufficient to reduce GFP levels to approximately half from more than 90% to 45%. This indicates that after a 24-hour differentiation pulse the differentiated state is irreversibly fixed in about 50% of NeFREC(g)s.

Figure 7:
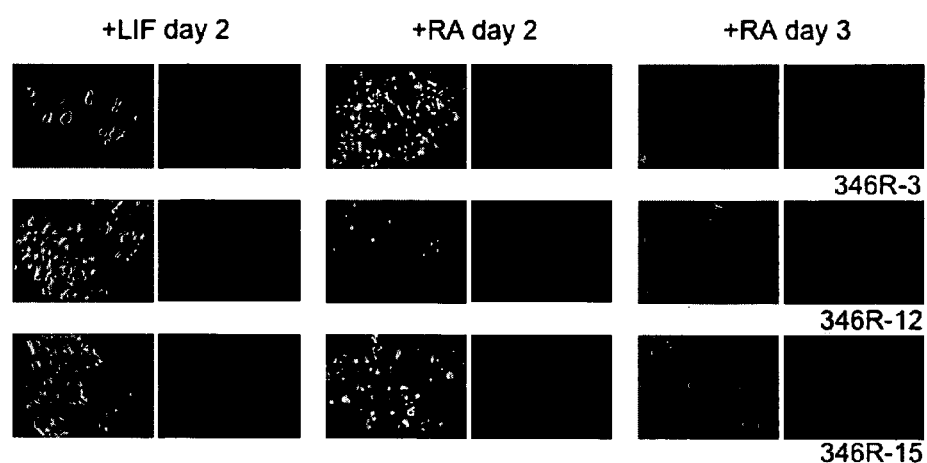
FIG. 7 shows that NeFREC(r) differentiate and downregulate Nanog/DsRedExpress in response to retinoic acid. Microscopy pictures of three NeFREC(r) clones shows that they express Nanog/DsRedExpress under self-renewal condition (+LIF) and downregulate Nanog/DsRedExpress upon RA-induced differentiation (compare cell morphology between +LIF and +RA).

NeFREC(r). For testing RFP reporter expression upon RA induced differentiation, similar experiments as shown in example 3 with NeFREC(g) were performed. 1.0 µM RA was added to 3 individual NeFREC(r) clones to demonstrate that down-regulation of RFP expression correlates with RA treatment. RFP expression in cells was examined by fluorescent microscopy and bright field and fluorescent pictures were taken at indicated time points. FIG. 7 shows that NeFREC(r) are expressing RFP/Nanog under self-renewal condition, i.e., in the presence of LIF. RA treatment induces differentiation and shutdown of Nanog expression and, hence, RFP expression is dramatically reduced by day 3. This demonstrates that RFP can also be used to monitor endogenous Nanog gene expression in ES cells. NeFREC(r) clones find use in combination with screens that include GFP as a reporter.

Example 3 shows that NeFRECs differentiate in response to RA treatment. The fast downregulation of GFP or RFP fluorescence in these cells correlates with endogenous Nanog expression (shown for NeFREC(g)). This Example demonstrates that NeFRECs serve as a useful, easy-handable and convenient tool for chemical genomics.

Example 4

NeFREC(g) can Differentiate to Ectoderm, Endoderm and Mesoderm Lineages During Embryoid Body Formation ES cells display the ability to differentiate into cells of ectoderm, endoderm and mesoderm lineage in culture. One method to initiate ES cell differentiation is to allow ES cells to aggregate and form three-dimensional colonies known as EBs (Martin and Evans, 1975. PNAS 72:1441-1445; Doetschman et al., 1985 J. Embryol. Exp. Morphol. 87:27-45). This method offers the advantage of enhancing cell-cell interactions in a three-dimensional structure that may better mimic developmental processes in vivo than any two-dimensional culture system. Mesoderm induction is characterized by the expression of Brachyury/T (Wilkinson et al., 1990 Nature 343:657-658). Gata4 and Sparc mark definitive endoderm (Arceci et al., supra; Mason et al., 1986. EMBO J. 5:1465-1472) while Fgf5 defines ectoderm (Haub and Goldfarb, 1991. Development 112:397-406; Hebert et al., Development 112:407-415). Nestin is a marker for neural precursor cells (Okabe et al., 1996. Mech. Dev. 59:89-102).

Figure 8:
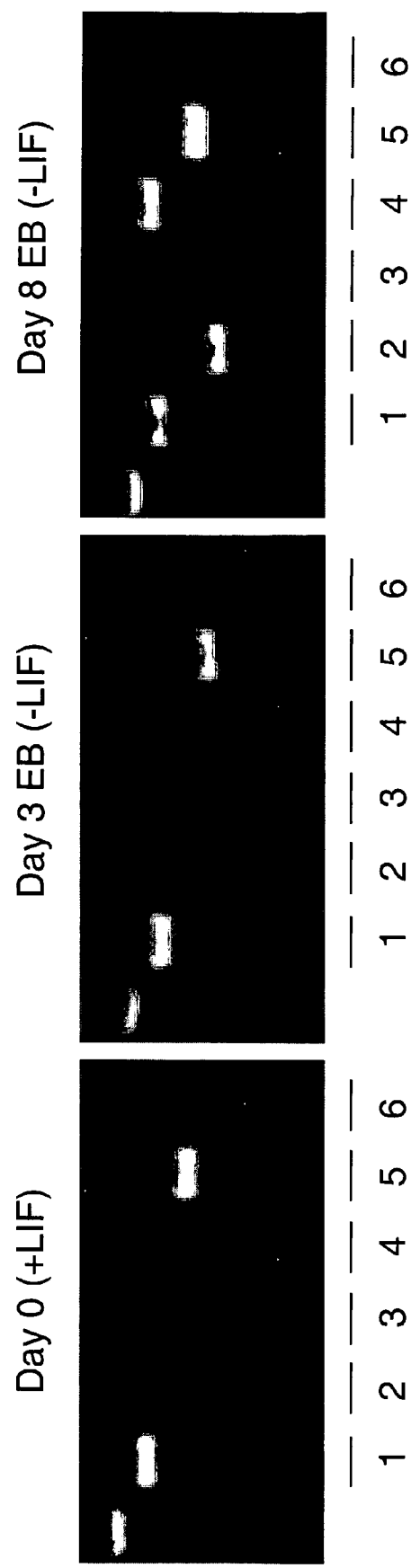
FIG. 8 shows that NeFREC(g) differentiate into all three germ lineages. RT-PCR analysis of lineage gene expression in NeFREC(g) (Day 0 +LIF), three-day (Day 3 EB−LIF) and eight-day differentiated EBs (Day 8 EB−LIF). 1, Eef1b (loading control); 2, Brachyury (mesoderm); 3, Fgf5 (ectoderm); 4, Gata4, (endoderm); 5, Sparc (endoderm); 6, Nestin (neural precursors).

In order to analyze whether NeFREC(g) can generate cells of all three germ layers, ectoderm, endoderm and mesoderm, during EB formation and differentiation, the appearance of lineage specific mRNAs was investigated by RT-PCR at day 3 and 8 of culture (FIG. 8). The following primers were used to detect mesoderm with Brachyury/T 5'-CATGTACTCTTTCTTGCTGG-3' (SEQ ID NO:19) and 5'-GGTCTCGGGAAAGCAGTGGC-3' (SEQ ID NO:20), endoderm with Gata4 5'-GCCTGTATGTAATGCCTGCG-3' (SEQ ID NO:21) and 5'-CCGAGCAGGAATTTGAAGAGG-3' (SEQ ID NO:22) and Sparc 5'-ATGAGGGCCTGGATCTTCTTTC-3' (SEQ ID NO:23) and 5'-GGAAGAGTCGAAGGTCTTGTTGTC-3' (SEQ ID NO:24), ectoderm with Fgf5 5'-AAAGTCAATGGCTCCCACGAA-3' (SEQ ID NO:25) and 5'-CTTCAGTCTGTACTTCACTGG-3' (SEQ ID NO:26) and neural precursor cells with Nestin 5'-AGATCGCTCAGATCCTGGAA-3' (SEQ ID NO:27) and 5'-GGGTTCTGGCCTTAAGGAAT-3' (SEQ ID NO:28). Eef1b was used as loading control (5'-TTACCTGGCGGACAAGAGCT-3' (SEQ ID NO:29) and 5'-CCAATTTAGAGGAGCCCCACA-3' (SEQ ID NO:30)). The results in FIG. 8 show that during EB formation and differentiation all lineages are induced at varying degrees by day 3 and even stronger by day 8.

Example 4 demonstrates that NeFREC(g) have the capacity to differentiate into cells of the three germ layers mesoderm, endoderm and ectoderm, including neural precursors and, hence, are pluripotent, a hallmark of ES cells.

Example 5

Downregulation of GFP of Serum-free Adapted NeFREC(g), NeFREC(g)-SF, Upon Removal of the Factors LIF and Bmp4

Maintenance of ES cells in serum-free culture conditions bears the advantage that factors required for self-renewal, such as LIF and Bmp4, or for specific lineage differentiation, such as Activin, can be tightly regulated. The NeFREC(g) line was adapted to serum-free culture condition. Its designated name is NeFREC(g)-SF. FIG. 9A shows that NeFREC(g)-SF maintain Nanog/GFP to a high percentage (94.8%) in ES-SF and lose Nanog/GFP relatively rapidly upon omission of both factors LIF and Bmp4 from the medium (33.5% Nanog/GFP+ cells by day 2). Nanog/GFP is also downregulated by omission of LIF alone. The kinetic is, however, slower and is down to 70.9% by day 2 and 47.3% by day 3 (FIG. 9B).

Example 5 shows that NeFREC(g)-SF downregulate Nanog/GFP by omission of LIF and Bmp4 or LIF alone. Nanog/GFP downregulation is faster when both LIF and Bmp4 are omitted from the medium and is similar to the downregulation kinetics of NeFREC(g) stimulated to differentiate by RA. This Example shows that NeFREC(g)-SF is a useful tool in chemical genomics or genetic screens that require tight regulation of the induction of differentiation in time or of the differentiation or self-renewal conditions (see Example 6-8).

Example 6

Chemical Genomics Using NeFRECs

Chemical genomics aims to discover small molecules and chemical compounds that affect biological processes through perturbation of protein function. Self-renewal and differentiation, a hallmark property of stem cells, are main biological processes in cell development. ES cells are characterized by an extensive in vitro self-renewal ability and their capacity to differentiate into all three germ layers and germ cells. For these reasons ES cells are an ideal cell source for chemical genomics.

To validate the use of NeFRECs as an easy reporter cell in chemical genomics proof-of-principle studies were performed with several compounds that are known to show effects on ES cell self-renewal and differentiation or were previously tested in early embryonic development and cancer therapy. The compounds included in the experiment were RA (Sigma, Cat# R2625), Trichostatin A (TSA, Sigma, Cat# T8552, a histone deacetylase (HDAC) inhibitor), Ly294002, (CALBIOCHEM, Cat# 440202, a phosphatidylinositol 3-kinase (PI3K) inhibitor), Rapamycin (Rapa, Sigma, Cat# R0395, an inhibitor of mTOR), PD98059 (CALBIOCHEM, Cat# 513000, a MAP kinase (MAPK) inhibitor), 5-aza-2'-deoxycytidine (AZA, Sigma, Cat# A3656, an inhibitor of DNA methyltransferases). AZA has been used in clinical therapy for cancer treatment and a recent study showed that it could prevent ES cell differentiation (Takayama et al., 2004. Biochem. Biophys. Res. Commun. 323:86-90).

Figure 10:
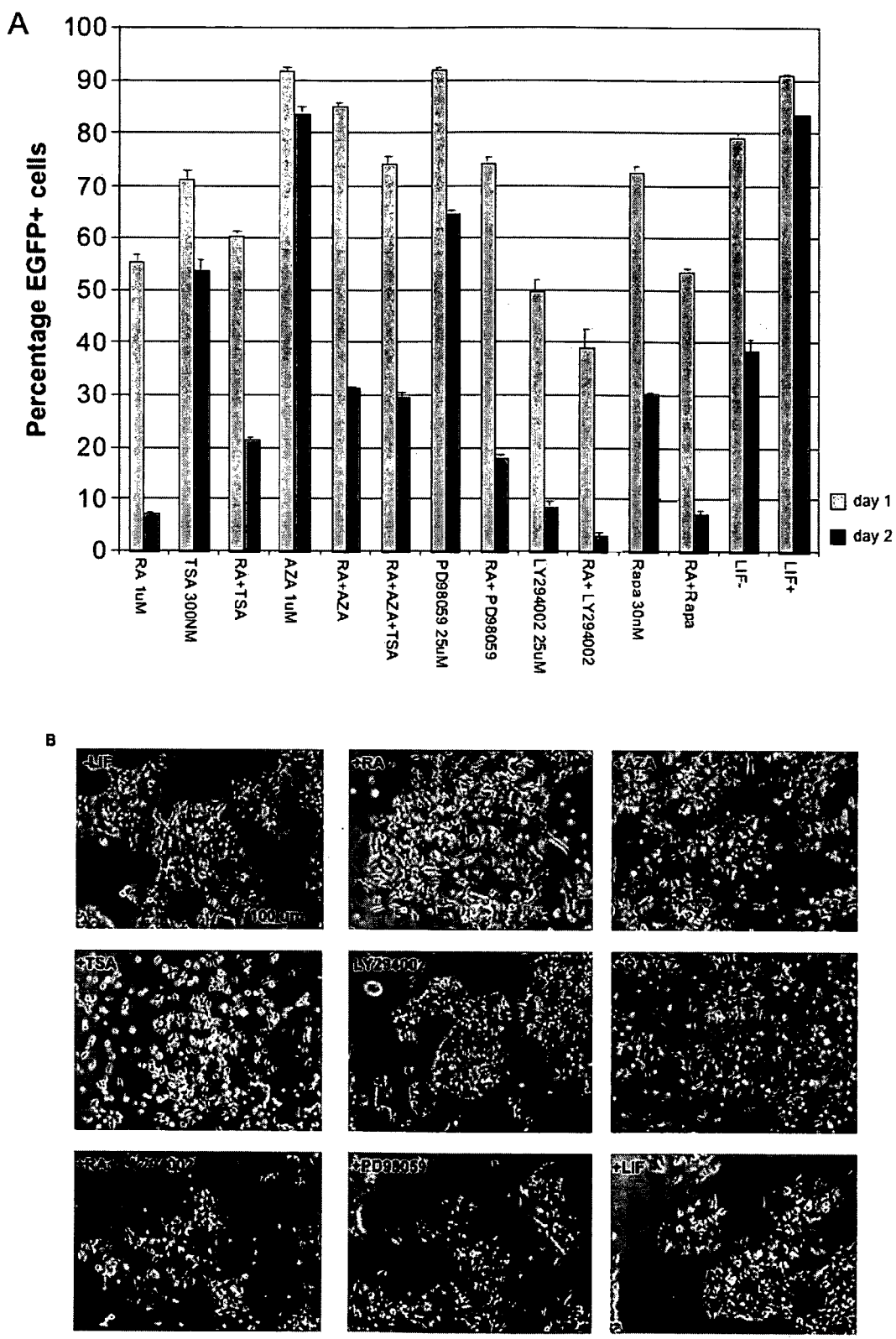
FIG. 10 shows a chemical genomics screen in NeFREC(g). A, NeFREC(g) were treated with various chemical compounds in ES medium without LIF and analyzed for Nanog/GFP expression by flow cytometry after one and two days. B, Cell morphology of NeFREC(g) after treatment with various chemical compounds for two days. C, NeFREC(g) are incubated with TSA at indicated concentrations for 24 hours and then treated with 1 µM RA (day 0 to 2).
Figure 10:
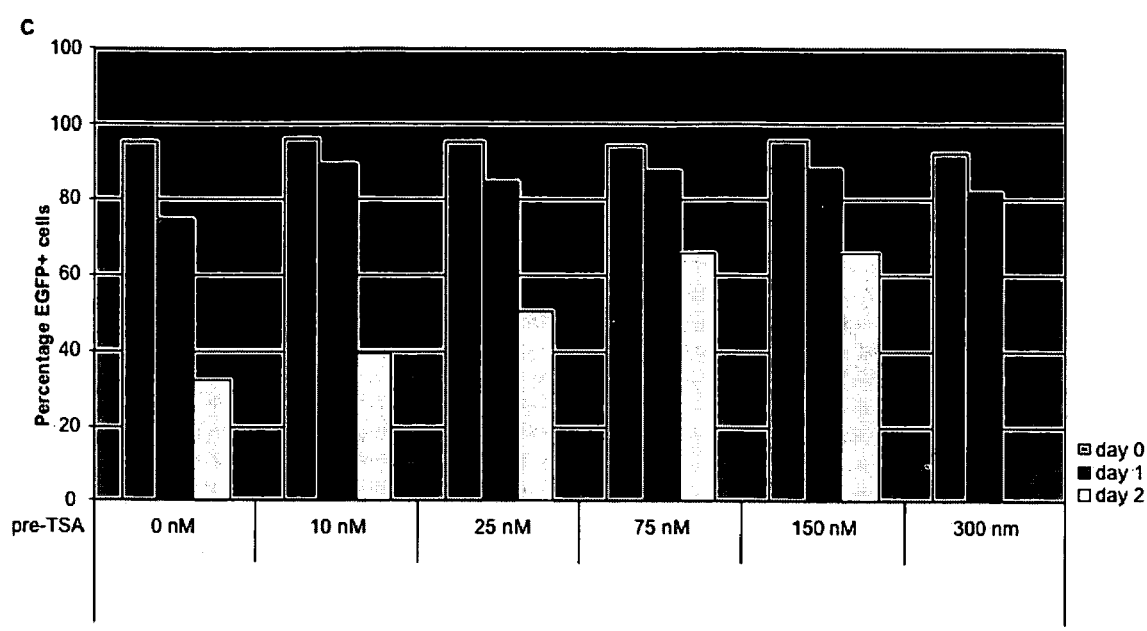

For the chemical genomics screen $2.5 \times 10^4$ cells in 0.5 ml ES medium were plated per 24-well the day before treatment. Medium without LIF supplemented with the different compounds at indicated concentrations was added 24 hrs post-plating. Medium was changed daily. Nanog/GFP levels for each sample were measured by flow cytometry one and two days post drug treatment. Average percentages of Nanog/ GFP+ cells were calculated from duplicate samples (FIG. 10A). Recent studies showed that PI3K activity is required for ES cell self-renewal and that inhibition of PI3K causes loss of self-renewal and, hence, results in differentiation (Jirmanova et al., 2002. Oncogene 21:5515-5528; Pahling et al., 2004. J. Bio. Chem. 279:48063-48070). This result was confirmed using the cell lines of the present invention. Ly294002 induces downregulation of GFP with similar kinetic as does RA. Combinatorial compound experiments revealed a minor additive effect of RA and LY294002 in terms of downregulation of Nanog/GFP expression. This indicates that the RA and PI3K intracellular signaling pathways work somewhat independent of each other and indicates that Nanog may be regulated in part by the PI3K pathway to maintain ES cell identity. Addition of Rapa to ES medium without LIF did not prevent Nanog/GFP downregulation and therefore ES cell differentiation. AZA, TSA and PD98059 blocked or delayed ES cell differentiation induced by the omission of LIF from the ES medium as demonstrated by higher Nanog/GFP expression compared to the ES medium minus LIF culture sample (FIG. 10A). In addition, these three agents also delay RA-induced Nanog/GFP downregulation in ES cells when compared to RA-induced differentiation condition.

Changes in cell morphology for the individual treatments on day 2 of treatment are shown in FIG. 10B. Addition of RA, LY294002 or PD98059 to the cultures has different effects on ES cell colony morphology. RA treated cells show differentiated cell morphology while LY294002 or PD98059 treated cells look more like NeFREC(g) cultured in ES medium alone.

A more detailed analysis of a combinatorial RA and TSA treatment is shown in FIG. 10C. In brief, $2.5 \times 10^4$ cells were plated in 0.5 ml ES medium. The HDAC inhibitor TSA was added at various concentrations 24 hours post-plating. One day after TSA treatment, medium was changed to ES medium without LIF plus 1.0 µM RA (indicated as day 0). Medium was changed and Nanog/GFP expression monitored by flow cytometry on a daily basis. RA-induced downregulation of Nanog/GFP is markedly reduced with TSA-concentrations higher than 75 nM. 75 nM TSA rescued Nanog/GFP levels by more than 50% by day 2. TSA, as well as AZA, can cause cell death at too high concentrations as indicated by floating cells in culture. 300 nM TSA is sufficient to kill all ES cells by day 3 of culture, and, hence, no Nanog/GFP expression data was collected.

This example demonstrates that NeFRECs are suitable for chemical genomics, including combinatorial compound screens. Measuring fluorescent reporter levels and visualizing cell morphology are easy and rapid and give an impression of the functional role of the compound in ES cell maintenance and differentiation. In addition, the protein target of interesting compounds, if unknown, can be determined by in situ proteome reactivity profiling (Evans et al., 2005. Nat. Biotechnol. 23:1303-1307).

Example 7

Genetic Screen to Analyze Self-renewal Versus Differentiation Fates Using NeFREC(g) or NeFREC(g)-SF Identification of factors regulation cell fate decisions by classical means, i.e., gene knockouts, is complicated and time-consuming. Gain-of-function screens are one path for rapid and direct validation of candidate genes. This avenue has led to the identification of the homeobox gene Nanog, necessary to maintain ES cells (Chambers et al., supra 2003. Cell 113: 643-655) and of a Wnt antagonist that induces ES cell differentiation to neural progenitors (Aubert et al., 2002. Nat. Biotechnol. 20:1240-1245). RNA interference is a novel rapid method to identify genes regulating cell fate decisions by loss-of-function (Hannon et al., 2002 Nature 418:244-251; Paddison and Hannon, 2003. Curr. Opin. Mol. Ther. 5:217-224).

Figure 11:
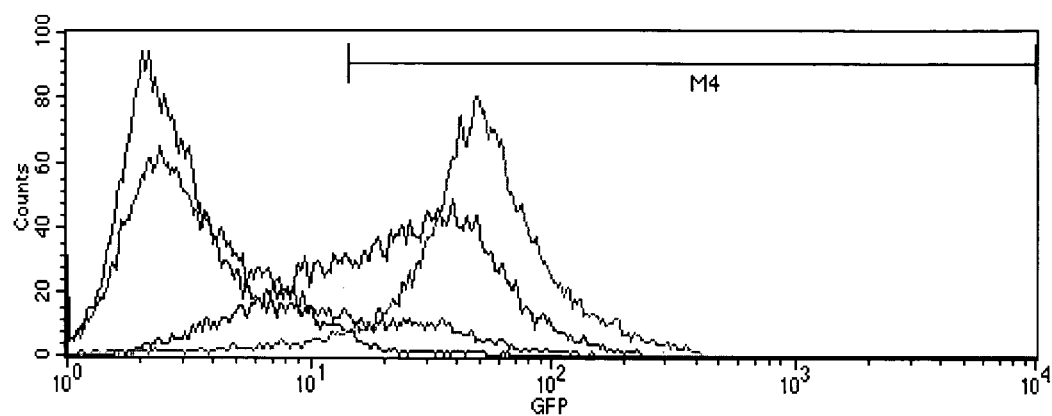
FIG. 11 shows downregulation of Nanog/GFP in NeFREC(g) by RNA shRNA against GFP and Pou5f1. A, NeFREC(g) in ES medium were transfected with different concentrations of RNA shRNA against GFP (0 pmole; 0.625 pmole; 2.5 pmole; 10 pmole). B, NeFREC(g) in ES medium were transfected with 15 pmole of RNA shRNA against Pou5f1 or GFP. C, NeFREC(g)-SF grown in SF-ES medium were transfected with 15 pmole of RNA shRNA against Pou5f1 or GFP.

In order to demonstrate the usefulness of NeFRECs in genetic screens, a transient RNA interference protocol was applied. RNA shRNA against GFP (5'-AGCCACAACGUC-UAUAUCAUGGCCGACAAGUUGGCU-UGUCGGCCAUGAUA UAGACGUUGUGGCUGU-3'; SEQ ID NO:31) was transfected into NeFREC(g) as described in Example 1. Ten pmole of RNA shRNA against GFP reduced Nanog/GFP reporter expression in NeFREC(g) from 85.8% down to 18% 72 hours post-transfection (FIG. 11A). The reduction in Nanog/GFP fluorescence is RNA shRNA concentration-dependent.

The transcription factor Pou5f1 is required for ES cell maintenance and when reduced by more than 50% of wild-type levels results in differentiation towards trophectodermal cells (Niwa et al., 2000 Nat. Genet. 24:372-376). Therefore, 10 pmole of RNA shRNA against Pou5f1 (5'-GCAGCU-CAGCCUUAAGAACAUGUGUAAGCUUUG-GAGCUUACACAUGUUCU UAAGGCUGAGCUGCAA-3'; SEQ ID NO:32) was transfected into NeFREC(g). By three days RNA shRNA against Pou5f1 reduced Nanog/GFP expression from 90.9% to 73.1% while RNA shRNA against GFP resulted in 21.2% of NeFREC(g) bearing Nanog/GFP (FIG. 11B). Similar results were seen with NeFREC(g)-SF (FIG. 11C). RNA shRNA against Pou5f1 reduced Nanog/GFP levels from 94.8% to 68.5% by day 2. RNA shRNA against EGFP decreased Nanog/GFP fluorescence to 14.1%.

This Example demonstrates that NeFRECs are an ideal tool for easy and rapid loss-of function approaches to identify regulatory molecules involved in ES cell self-renewal and lineage differentiation. Loss-of-function experiments can be performed in a stable form using vector-based strategies or transiently using oligonucleotide-based strategies.

Example 8

Isolation of Nanog+ Cells

Figure 12:
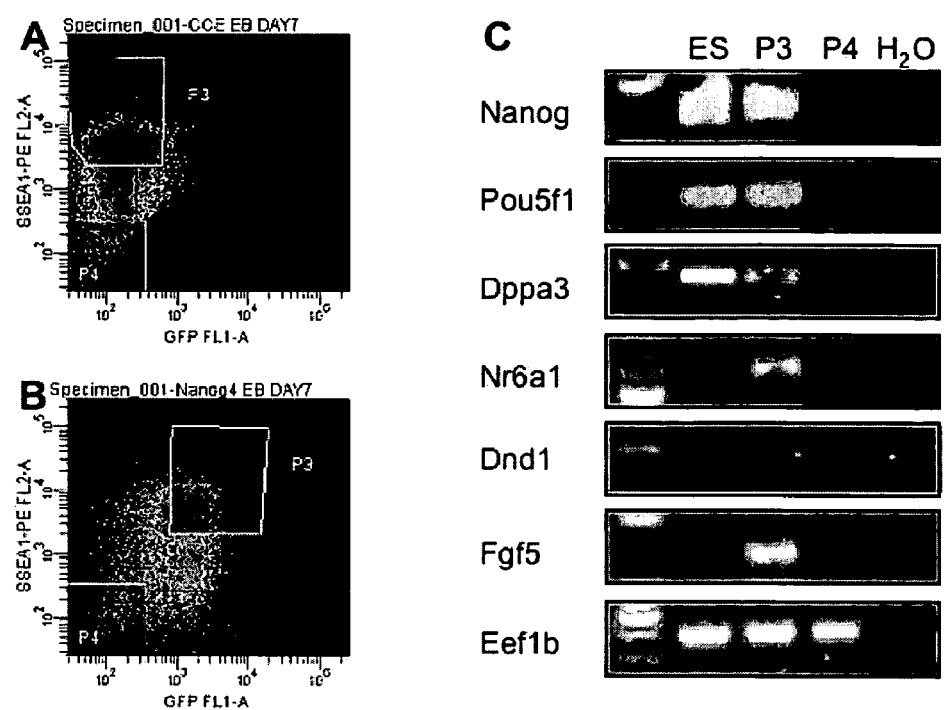
FIG. 12 shows FACS and molecular germ cell-profile of cells forming and differentiating in EBs. A and B, CCE ES cells (A) and NeFREC(g) (B) were aggregated to form EBs and differentiated for 7 days and then analyzed for their expression of the cell surface marker SSEA1 and Nanog/GFP, for NeFREC(g) only, by flow cytometry. C, RT-PCR analysis for the indicated molecular markers was performed on cDNAs generated from sorted SSEA1$^+$Nanog/GFP$^+$ (P3) and SSEA1$^-$Nanog/GFP$^-$ (P4) cell population (shown in B).

Nanog has been shown to be essential for the integrity of ES cells and is expressed in the epiblast in the early embryo and in developing germ cells (Mitsui et al., supra; Chambers et al., supra; Hatano et al., 2005. Mech. Dev. 122:67-79; Yamaguchi et al., 2005. Gene Expr. Patterns 5:639-646). To determine if Nanog+ cells could be isolated based on GFP expression and whether this population is enriched in germ cell precursors, NeFREC(g) and wild-type CCE ES cells were aggregated and differentiated in EB cultures for 7 days. Nanog/GFP expression was compared with that of the stage-specific embryonic antigen 1 (SSEA1) which is expressed on ES cells and on germ cells (Solter and Knowles, 1978. PNAS 75:5565-5569; Matsui et al., 1992 Cell 70:841-847) and was previously used to isolate cells with germ cell potential (Geijsen et al., 2003 Nature 427:148-154). Therefore, EBs were harvested and incubated with 0.1% Collagenase IV (Sigma), 0.2% Hyaluronidase (Sigma) and 50 U/ml DNAse (Sigma) in IMDM at 37° C. for 20 min with periodic shaking. Enzyme-free dissociation buffer was added (Invitrogen/Gibco) and the cells were centrifuged at 300 g at 4° C. for 5 min. This dissociation step was repeated once. Dissociated cells were resuspended in PBS/5% FCS and stained with SSEA1 antibody (1:100 of concentrate, clone name: MC-480, Developmental Studies Hybridoma Bank, developed under the auspices of the NICHD and maintained by The University of Iowa, Department of Biological Sciences, Iowa City) at 4° C. for 30 minutes. Cells were washed with PBS/5% FCS and stained with PE-conjugated anti-mouse IgM (1:100, clone III/41, eBioscience). Cells were washed and resuspended in PBS/5% FSC containing 1 µg/ml propidium iodide (Molecular Probes). Cells were sorted according to SSEA1 and Nanog/GFP⁻ expression from day seven EBs (FIGS. 12A and B). The FACS profiles show that almost all of the SSEA1⁺ cells also transcribe Nanog/GFP. Hence, sorting for Nanog/GFP alone results in a pure SSEA1⁺ population as used by Geijsen and coworkers to enrich for PGC. A similar FACS profile is seen with day 8 EBs.

Primordial/embryonic germ cells (PGCs/EG cells) and ES cells are largely indistinguishable by molecular markers. Both express the cell surface molecule SSEA1, the transcription factors Nanog and Pou5f1 and Dppa3. Dppa3 is known and widely used as the earliest PGC marker (Sato et al., 2002. Mech Dev. 113:91-94). Few genetic markers distinguish PGCs from ES cells. Nr6a1/Gcnf is expressed in the germ lineage and restricts expression of Pou5f1 during development (Fuhrmann et al., 2001. Dev Cell 1:377-387; Yang et al., 2003. Biol Reprod. 68:1620-1630). In mice, the Ter mutation in the dead end gene, Dnd1, causes PGC loss and is a potent modifier of spontaneous germ cell tumor susceptibility (Youngren et al., 2005. Nature 435:360-364). Founder PGCs emerge at the interface of the most proximal edge of the epiblast that is likely in direct contact with the extra-embryonic ectoderm (Ohinata et al., 2005. Nature 436:207-213). A marker for the primitive ectoderm/epiblast is Fgf5. However, its expression in PGCs or its precursor cells has not yet been investigated.

RT-PCR for Nanog (5'-AGGCTTTGGAGACAGTGAG-GTGC-3'; SEQ ID NO:33 and 5'-TACCCTCAAACTCCTG-GTCCTTC-3'; SEQ ID NO:34), Pou5f1 (5'-GAACCTG-GCTAAGCTTCCAA-3'; SEQ ID NO:35 and 5'-GAAGCGACAGATGGTGGTCT-3'; SEQ ID NO:36), Dppa3 (5'-GATGAAGAGGACGCTTTGGA-3'; SEQ ID NO:37 and 5'-GATTTCCCAGCACCAGAAAA-3'; SEQ ID NO:38), Nr6a1 (5'-GTGGAAGACCAGGACGACGA-3'; SEQ ID NO:39 and 5'-CCTACTGGATGATAGTGTGG-3'; SEQ ID NO:40), Dnd1 (5'-TCCGCCTAATGATGACCTTC-3'; SEQ ID NO:41 and 5'-TCCCTGGTCTGGGTTAGTTG-3'; SEQ ID NO:42) and Fgf5 (5'-AAAGTCAATGGCTC-CCACGAA-3'; SEQ ID NO:43 and 5'-CTTCAGTCTGTACTTCACTGG-3'; SEQ ID NO:44) was conducted in order to define a molecular PGC-gene signature of the SSEA1⁻Nanog/GFP⁻ (P4) and SSEA1⁺Nanog/GFP⁺ (P3) populations (FIG. 12C). Amplification of Eef1b (5'-TTACCTGGCGGACAAGAGCT-3'; SEQ ID NO:45 and 5'-CCAATTTAGAGGAGCCCCACA-3'; SEQ ID NO:50) was performed as a template loading control. The PCR data confirmed that the SSEA1⁺Nanog⁺/GFP⁺ (P3) population was enriched in cells expressing Nanog, Pou5f1, Dppa3, Nr6a1, Dnd1 and Fgf5 while SSEA1⁻Nanog/GFP⁻ (P4) cells transcribe none of these markers (FIG. 12C). The results also indicate that Fgf5 is expressed by PGC founder cells and that the SSEA1⁺Nanog⁺/GFP⁺ EB population contains cells of multiple developmental lineage capabilities.

This Example shows that during EB formation and differentiation SSEA1 expression correlates well with that of Nanog/GFP. Hence, NeFRECs can be used to easily enrich for a SSEA1⁺ cell population in differentiating EBs without the time-consuming steps involved with EB dissociation and SSEA1 staining. In addition, Nanog/GFP⁺ cells of day 7 EBs transcribe genes specific for and, hence, are enriched for PGCs or their precursors.

Example 9

In vitro Germ Cell Development from NeFREC(g)

Figure 13:
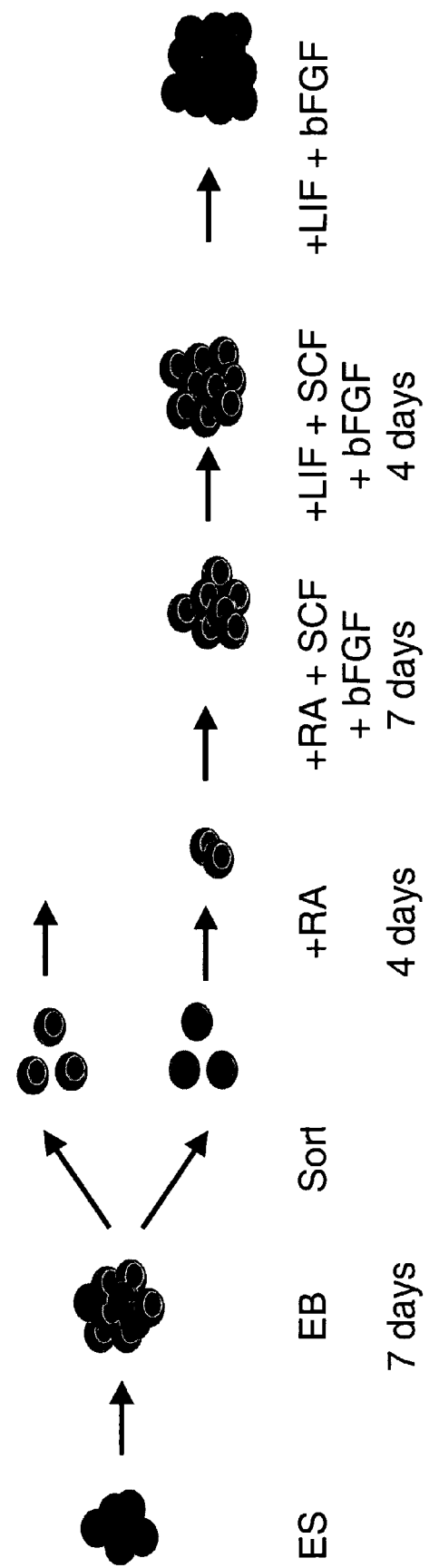
FIG. 13 shows a schematic view of the culture condition of the in vitro derivation of embryonic germ cells from NeFREC (g).
Figure 14:
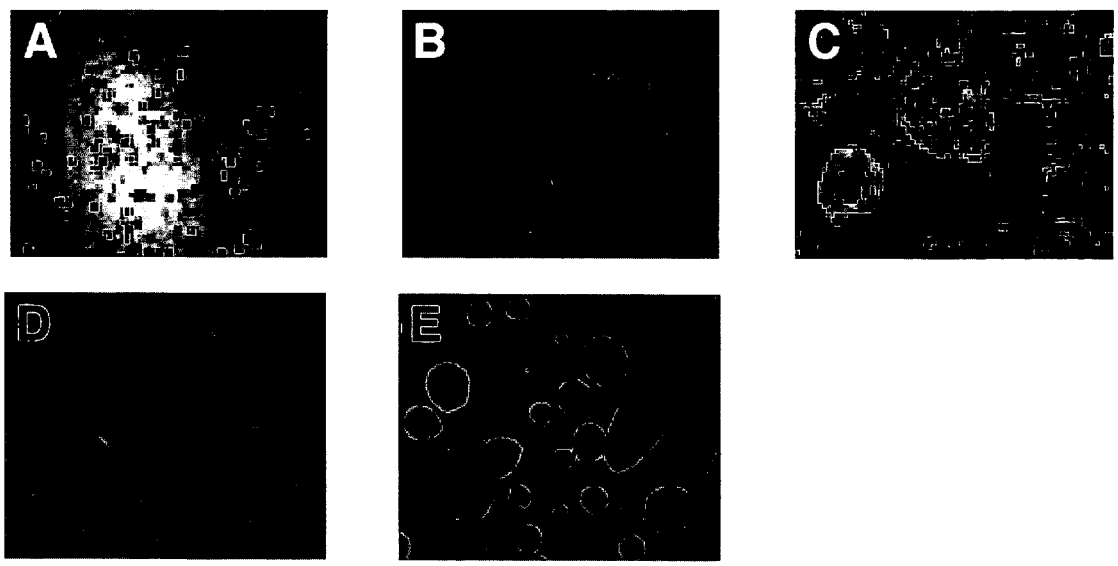
FIG. 14 shows that derivation of alkaline phosphatase-expressing germ cells from NeFREC(g) occurs via a Nanog/GFP⁻ developmental state. A, SSEA1⁻Nanog/GFP⁻ cells sorted from day 7 NeFEC(g)-derived EBs do not form PGC/EG cell colonies, while SSEA1⁺Nanog/GFP⁺ cells develop into colonies that are do not express Nanog/GFP (B, day 17 of culture), but eventually start to retranscribe Nanog/GFP as indicated by GFP fluorescence (C, overlay of brightfield and fluorescence picture at day 36 of culture). NeFREC(g) colonies are positive for alkaline phosphate activity (D) as are NeFREC(g)-derived EG cells (E).

PGCs are the embryonic founders of female and male gametes from which all sexually reproducing organisms arise. PGCs are totipotent, a characteristic that they share with ES cells. EG cells can be derived from migratory and gonadal PGCs up to E12.5. PGCs and EG cells are indistinguishable from ES cells with respect to known markers (see Example 8) as well as expression of alkaline phosphatase (Bernstine et al., 1973. PNAS 70:3899-3903). One exception is the erased status of genomic imprints in EG cells established from gonadal PGCs (Hajkova et al., 2002. Mech Dev. 117:15-23). Recently EG cells, spermatogonia and oocytes were derived from ES cells in vitro (Geijsen et al., 2003. Nature 427:148-154; Hübner et al., 2003. Science 300:1251-1256; Toyooka et al., PNAS 100:11457-11462). Geijsen and colleagues used the cell surface antigen SSEA1 to purify cells with PGC/EG cell potential from EBs. The cells were cultured on a feeder layer in the presence of RA. RA is an in vitro growth stimulus for PGCs (Koshimizu et al., 1995. Dev Bio. 168:683-685). The foregoing example shows that a germ cell-specific gene expression profile is manifested in the SSEA1⁺Nanog/GFP⁺ population of differentiating EBs. Therefore, it was investigated whether PGCs/EG cells could be derived from this population. SSEA1⁺Nanog/GFP⁺ (P3) and SSEA1⁻Nanog/GFP⁻ (P4) cells were sorted as described in Example 8 and shown in FIGS. 12A and B. The purified cells were placed on STO feeder cells in EB medium supplemented with 2 µM RA (see FIG. 13 for a schematic view of the culture system). Half of the medium was changed daily for the entire culture period. After 4 days, medium was changed to also contain 100 µg/ml stem cell factor (SCF, Peprotech) and 1 ng/ml basic fibroblast growth factor (bFGF, Peprotech) in addition to EB medium supplemented with 2 µM RA. SCF and bFGF have been shown to act as survival factors for PGC in vitro (Dolci et al., 1991. Nature 352:809-811; Godin et al., 1991. Nature. 352:807-809; Matsui et al., 1991. Nature 353:750-752; Matsui et al., 1992. Cell 70:841-847; Resnick et al., 1992. Nature 359:550-551). The cells were cultured in this medium for 7 days before it was changed to ES medium plus 100 µg/ml SCF and 1 ng/ml bFGF for an additional 4 days. At the end of the 15-day culture period no colonies grew from the SSEA1⁻Nanog/GFP⁻ population (FIG. 14A). Hence, this population has no detectable PGC cell potential. In contrast, individual colonies arose from the SSEA1⁺Nanog/GFP⁺ cell population. These colonies were picked and expanded in ES medium supplemented with 1 ng/ml bFGF to establish EG cell colonies (medium was changed on a daily basis). Nanog/GFP expression was lost during the initial culture period (FIG. 14B) and reappeared after expansion in ES medium plus bFGF (FIG. 14C). NeFREC(g)-derived EG cell colonies are positive for alkaline phosphatase activity (FIGS. 14 D and E).

Figure 15:
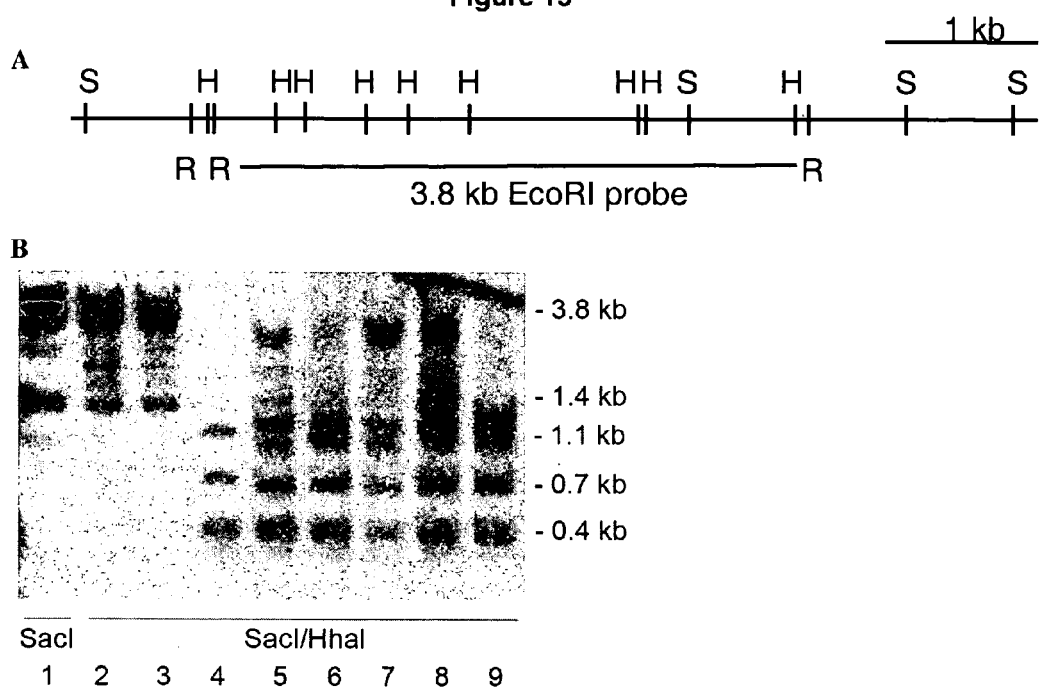
FIG. 15 shows imprint erasure in NeFREC(g)-derived EG cells. A, Graph showing the genomic locus of paternally imprinted H19. H, HhaI restriction site; R, EcoRI restriction site; and S, SacI restriction site. B, Southern blot analysis of genomic DNA digested with the indicated restriction enzymes. Lane 1 and 2, NeFREC(g); lane 3, Ainv15 (an non-NeFREC related ES cell line); lane 4, CCE ES cell-derived EG cell clone C1; lane 5, CCE ES cell-derived EG cell clone C5; lane 6, NeFREC(g)-derived EG cell clone N1; lane 7, NeFREC(g)-derived EG cell clone N4; lane 8, NeFREC(g)-derived EG cell clone N9; and lane 9, NeFREC(g)-derived EG cell clone N10b.

In order to show that NeFREC(g)-derived cell colonies are truly EG cells and not some remnant ES cells that survived the strong differentiation conditions, the clones were investigated to determine whether or not they erased the genomic imprint of the paternally inherited H19 locus. FIG. 15 shows Southern blot data of a few of the clones established. In contrast to ES cells, the two representative CCE ES cell-derived EG clones (lanes 4 and 5) and the 4 representative NeFREC(g)-derived EG clones (lanes 6-9) have the H19 imprint removed. All established CCE ES cell- or NeFREC (g)-derived EG cell clones have their H19 imprints removed, a few, however, only partially.

This Example demonstrates that NeFRECs can be used to isolate Nanog/GFP+ cells during EB formation and differentiation, that the purified cells have the capacity to develop into PGCs and EG cell colonies in vitro, and that these NeFREC-derived EG cell colonies erase their imprints efficiently.

Example 10

Generation of Transgenic Mice

The foregoing examples describe Nanog expression in pluripotent cells of mouse pre-implantation embryo and in proliferating and migrating PGC. In order to visualize, isolate and analyze cells which express Nanog in vivo, as well as to have a source of cells for nuclear reprogramming studies, i.e., cells that do not transcribe Nanog, but carry the Nanog/Fluorescent color reporter, which gets activate upon reprogramming (see Example 12), transgenic animals harboring GFP or RFP fluorescent reporters under Nanog regulatory elements were generated.

Figure 16:
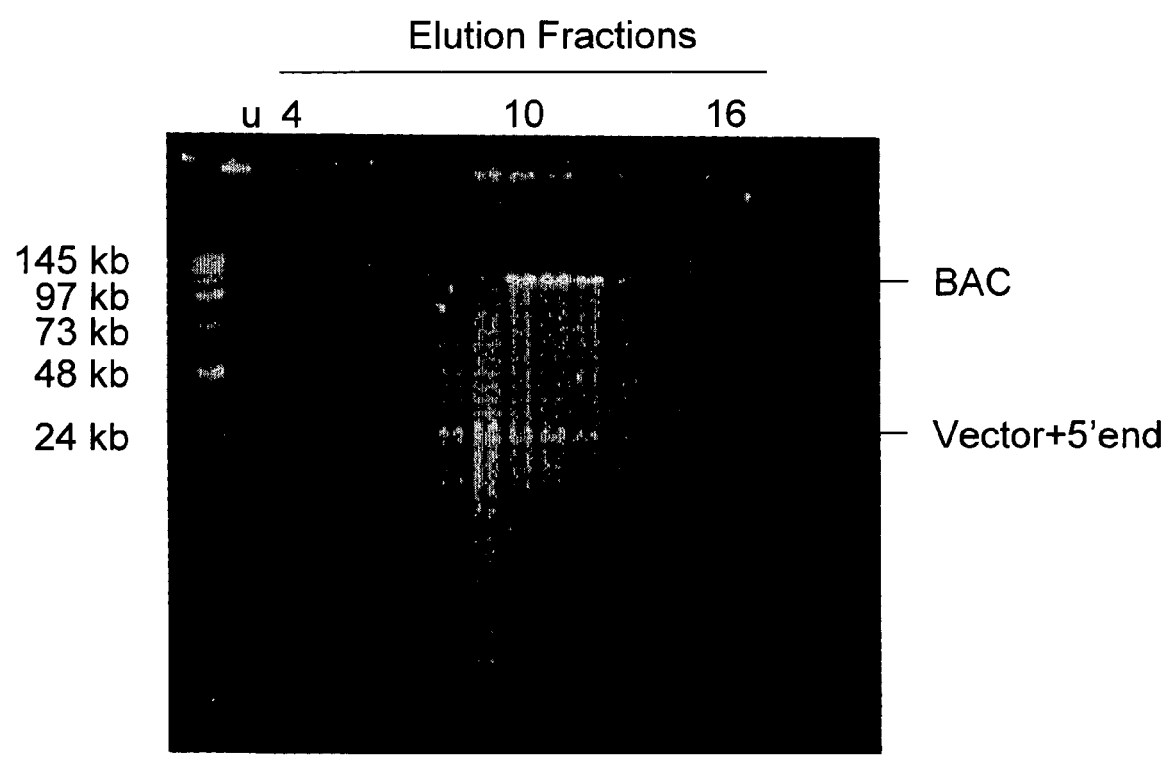
FIG. 16 shows a pulse-field gel of BsiWI digested Nanog/GFP BAC.

Nanog/GFP mice. For the generation of Nanog/GFP transgenic mice Nanog/HygEGFP BAC DNA was digested with BsiWI and isolated over Sepharose column. Briefly, a 5 ml plastic pipet with the cotton-wool plug pushed to the tip was filled with Sepharose CL4b (Sigma) up to 1 cm below the top. The column was equilibrated with 30 ml Injection Buffer (10 mM Tris-Cl pH7.4, 0.1 mM EDTA, 100 mM NaCl). 5 µl of 0.25% bromophenol blue was added to the digested DNA and loaded onto the column. Once the DNA entered the matrix 0.5 ml Injection Buffer was added and 0.5 ml aliquots collected until blue dye reached bottom of pipet. 40 µl of each fraction was run out on a 1% pulse field gel agarose (BioRad, Cat #162-0137) with 0.5× TBE as running buffer on a CHEF-DRII apparatus (Bio-Rad) with the following settings: Initial Switch Time: 1, Final Switch Time: 6, run at 6 V/cm. The gel was run for approximately 14 hours, stained with ethidium bromide, washed with water and visualized under UV (FIG. 16). Fractions chosen for oocyte injection (fractions 10 and 11) were submitted at a concentration of 2 ng/µl.

Nanog/RFP mice. In order to generate transgenic mice carrying the Nanog/DsRedExpress reporter, Nanog/RFP mice, 30 µg of plasmid 346R was digested with SpeI and XhoI and separated on a 0.75% UltraPureTM L.M.P. Agarose (Low Melting Point) gel (Invitrogen). The approximately 12 kb Nanog/DsRedExpress fragment was isolated, extracted 3 times by Phenol/Chloroform and once with Chloroform, and precipitated. Purified DNA was dissolved in 10 mM Tris-HCl.

DNA was injected into fertilized C57B1/6 oocytes by the Transgenic Core Facility in the Department of Molecular Biology, Princeton University according to standard protocol and the guidelines of the University's Institutional Animal Care and Use Committee.

Founder mice and subsequent offsprings were typed by tail-PCR for GFP using oligos 5'-ACGTAAACGGCCA-CAAGTTC-3' (SEQ ID NO:51) and 5'-TGCTCAGG-TAGTGGTTGTCG-3' (SEQ ID NO:52) or DsRedExpress using primers 5'-TCCAAGGTGTACGTGAAGCA-3' (SEQ ID NO:53) and 5'-TGGTGTAGTCCTCGTTGTGG-3' (SEQ ID NO:54).

Example 11

In vivo Nanog/Fluorescent Reporter Expression and Germ Cell Development

This example shows that Nanog/Fluorescent reporter mice can be used to easily visualize cells during embryonic development that express Nanog.

Figure 17:
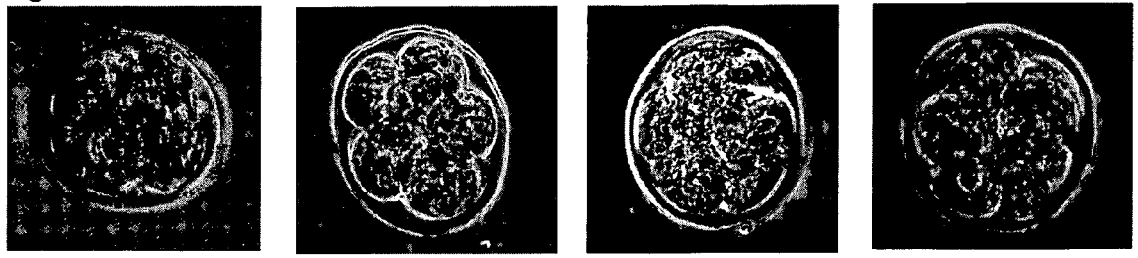
FIG. 17 shows expression of Nanog/RFP during mouse embryonic development. A, 4-, 6- and two 8-cell stage embryos do not transcribe Nanog/RFP. B, Nanog/RFP signal is detectable in the inner cell mass cells and weakly in some cells of the trophectoderm. C, The epiblast, but not extra embryonic mesoderm or primitive endoderm of E7.5 embryos is readily Nanog/RFP⁺. D and E, Nanog/RFP⁺ PGCs can be seen in the area of the hindgut in E8.5 (D) and E9 (E) embryos.
Figure 17:
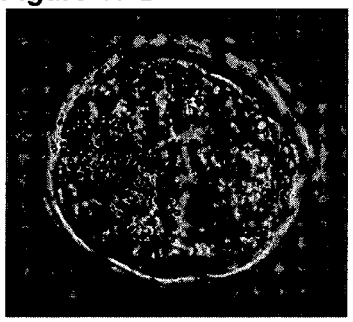
Figure 17:
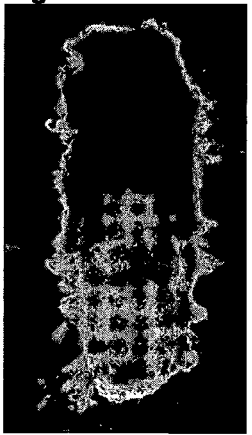

Wild-type females were time-mated with transgenic males, here Nanog/RFP mice, in the afternoon. The next morning was considered embryonic day 0.5 (E0.5) if females were plugged. In pre-implantation embryos no Nanog/RFP signal was found in all 2-cell to 8-cell stage embryos analyzed (FIG. 17A). Expression of Nanog/RFP was first observed in cells of morula-stage embryos. The inner cell mass (ICM) cells of blastocysts were strongly Nanog/RFP+ (FIG. 17B). Low-level expression was observed in trophectoderm. This may be remnant fluorescence due to the half-life of RFP. Nanog transcription should be restricted to cells of the ICM at the blastocyst-stage (Stumpf et al., 2005. Development 132:2093-2102). During early post-implantation development, Nanog/RFP+ cells were restricted to the epiblast of E6.5-E7.5 embryos (FIG. 17C). Strong Nanog/RFP signal was detectable at the interface of the most proximal edge of the epiblast that is likely in direct contact with the extra-embryonic ectoderm. PGC founder cells emerge in this region of the embryo (Ohinata et al., 2005. Nature 436:207-213). PGCs migrate through the hindgut and the dorsal mesentery to the developing gonad during E8-E10.5 of embryonic development. In E8.5 or E9 embryos Nanog/RFP+ cells are readily detectable in the region of the hindgut (FIGS. 17D and E).

This example shows that Nanog/Fluorescence reporter mice are an ideal tool to visualize Nanog-expressing cells during embryonic development. The mice also facilitate isolation of Nanog-transcribing cells for further cellular and molecular analysis. For example, PGCs of different developmental stages can be purified according to Nanog-expression and the cell's ability to reconstitute germ cell-deficient animals tested by transplantation. In addition, gene expression profiling of the diverse PGC populations can reveal unique molecular signatures of PGC development.

Example 12

Nuclear Reprogramming of Somatic Cells from Nanog/GFP Mice: Fusion of Thymocytes with ES Cells Understanding nuclear reprogramming of somatic cells has gained much interest because it may eventually be possible to directly convert adult somatic cells to a stem cell condition and hence the production of patient-tailored cell lines for the study and treatment of disease. Nuclear reprogramming can be achieved by nuclear transfer (Rideout et al., 2001. Science 293:1093-1098), creation of cell hybrids (Tada et al., 2001. Curr. Biol. 11:1553-1558) or incubation with cellular extracts (Taranger et al., 2005. Mol. Biol. Cell 16:5719-5739. Epub 2005 Sep. 29).

Figure 18:
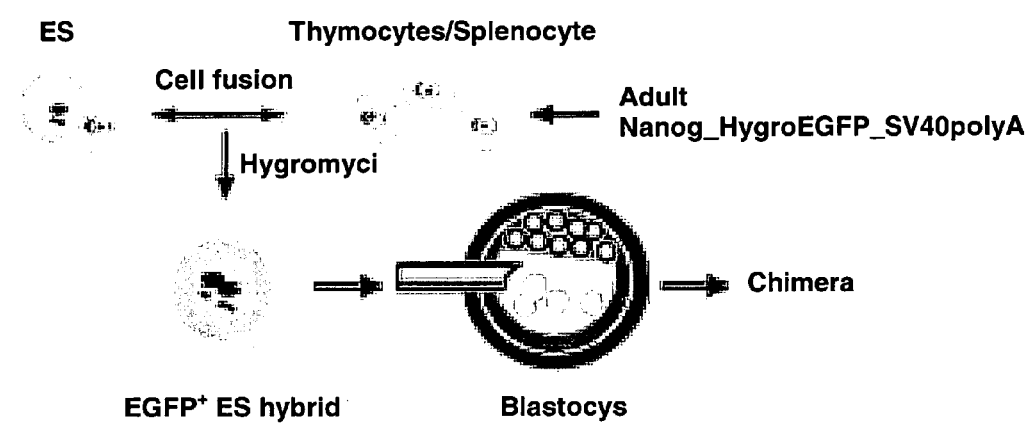
FIG. 18 shows reprogramming of Nanog/GFP in thymocytes by fusion with ES cells. A, schematic of reprogramming. B, visualization of fluorescence in reprogrammed cells.
Figure 18:
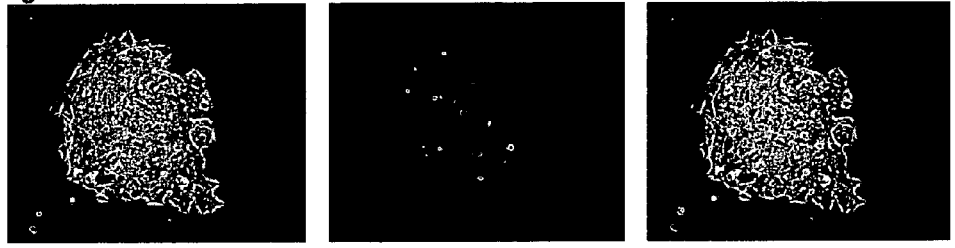

To demonstrate the use of NeFRECs to visualize reprogrammed somatic cells, $7.5 \times 10^6$ thymocytes from Nanog/GFP transgenic mice were fused to with wild-type ES cells in a 5 to 1 ratio using polyethylene glycol solution (Sigma) according to standard protocol. Cells were plated onto gelatin-coated dishes in ES medium. Hygromycin selection (250 µg/ml) was started 48 hours after plating. Growth medium was changed daily. After 10 to 14 days individual colonies were picked and expanded. FIG. 18 shows one colony that survived selection and expansion.

This example demonstrates the Nanog/fluorescent reporter mice provide a source for cells such as thymocytes that can be used to easily visualize reprogrammed cells.

All publications and patents mentioned in the above specification are herein incorporated by reference. Various modifications and variations of the described method and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a bacterial artificial chromosome (BAC), wherein said BAC comprises
   a) a reporter gene having a 5' end and a 3' end,
   b) a first Nanog gene regulatory sequence operably linked to said 5' end of said reporter gene, wherein said first Nanog gene regulatory sequence is produced by amplification of a mouse DNA sequence using a first PCR forward primer (SEQ ID NO:3) and a first PCR reverse primer (SEQ ID NO:4) in a first polymerase chain reaction, and
   c) a second Nanog gene regulatory sequence operably linked to said 3' end of said reporter gene, wherein said second Nanog gene regulatory sequence is produced by amplification of a mouse DNA sequence using a second PCR forward primer (SEQ ID NO:5) and a second PCR reverse primer (SEQ ID NO:6) in a second polymerase chain reaction,
   wherein the level of expression of said reporter gene is lower in a differentiated mouse embryonic stem cell comprising said BAC compared to the level of expression of said reporter gene in an undifferentiated mouse embryonic stem cell comprising said BAC.

2. The composition of claim 1, wherein said reporter gene encodes a fluorescent protein.

3. The composition of claim 2, wherein said fluorescent protein is selected from the group consisting of green and red fluorescent protein.

4. The composition of claim 1, wherein said BAC further comprises a selectable marker.

5. An isolated embryonic stem cell comprising the composition of claim 1.

6. The isolated embryonic stem cell of claim 5, wherein said isolated embryonic stem cell is selected from the group consisting of an isolated mouse embryonic stem cell and an isolated human embryonic stem cell.

7. An isolated embryonic germ cell comprising the composition of claim 1.

8. An isolated primordial germ cell comprising the composition of claim 1.

9. A composition comprising a portion of a Nanog gene, said portion is produced by amplification of a mouse DNA sequence using a first PCR forward primer (SEQ ID NO:3) and first PCR reverse primer (SEQ ID NO:4) in a polymerase chain reaction.

10. A composition comprising a portion of a Nanog gene, said portion is produced by amplification of a mouse DNA sequence using a first PCR forward primer (SEQ ID NO:5) and first PCR reverse primer (SEQ ID NO:6).

11. The composition of claim 1, wherein said first Nanog gene regulatory sequence comprises a nucleotide sequence from nucleotide 9 to nucleotide 539 of SEQ ID NO:55.

12. The composition of claim 1, wherein said second Nanog gene regulatory sequence comprises a nucleotide sequence from nucleotide 2523 to nucleotide 3089 of SEQ ID NO:55.

13. A composition comprising a bacterial artificial chromosome (BAC), wherein said BAC comprises
  a) a reporter gene having a 5' end and a 3' end,
  b) a first Nanog gene regulatory sequence from nucleotide 9 to nucleotide 539 of SEQ ID NO:55, wherein said first Nanog gene regulatory sequence is operably linked to said 5' end of said reporter gene, and
  c) a second Nanog gene regulatory sequence from nucleotide 2523 to nucleotide 3089 of SEQ ID NO:55, wherein said second Nanog gene regulatory sequence is operably linked to said 3' end of said reporter gene.

14. The composition of claim 13, wherein said reporter gene encodes a fluorescent protein.

15. The composition of claim 13, wherein said fluorescent protein is selected from the group consisting of green fluorescent protein and red fluorescent protein.

16. The composition of claim 13, wherein said BAC further comprises a selectable marker.

17. An isolated embryonic stem cell comprising the composition of claim 13.

18. The isolated embryonic stem cell of claim 17, wherein said isolated embryonic stem cell is selected from the group consisting of an isolated mouse embryonic stem cell and an isolated human embryonic stem cell.

19. An isolated embryonic germ cell comprising the composition of claim 13.

20. An isolated primordial germ cell comprising the composition of claim 13.

21. A composition comprising a nucleic acid consisting essentially of nucleotide 9 to nucleotide 539 of SEQ ID NO:55.

22. A composition comprising a nucleic acid consisting essentially of nucleotide 2523 to nucleotide 3089 of SEQ ID NO:55.

* * * * *

SEQUENCE LISTING

```
<160> NUMBER OF SEQ ID NOS: 55

<210> SEQ ID NO 1
<211> LENGTH: 34
<212> TYPE: DNA
<213> ORGANISM: Artificial Sequence
<220> FEATURE:
<223> OTHER INFORMATION: Synthetic

<400> SEQUENCE: 1
aaacccgggg ccgccaccat gaaaaagcct gaac                                34

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
gtcgcggccg ctttacttgt acag                                          24

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
cccggcgcgc cccaatgtga agagcaagca a                                  31

<210> SEQ ID NO 4
<211> LENGTH: 29
<212> TYPE: DNA
<213> ORGANISM: Artificial Sequence
<220> FEATURE:
<223> OTHER INFORMATION: Synthetic

<400> SEQUENCE: 4
agtcccgggc agccttccca cagaaagag                                     29

<210> SEQ ID NO 5
<211> LENGTH: 31
<212> TYPE: DNA
<213> ORGANISM: Artificial Sequence
<220> FEATURE:
<223> OTHER INFORMATION: Synthetic

<400> SEQUENCE: 5
gcgttaatta agaggaagca tcgaattctg g                                  31

<210> SEQ ID NO 6
<211> LENGTH: 31
<212> TYPE: DNA
```

```
<213> ORGANISM: Artificial Sequence
<220> FEATURE:
<223> OTHER INFORMATION: Synthetic

<400> SEQUENCE: 6
actggccggc cgtttggaag gagcactgag c                              31

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tgaacttgtg gccgtttacg                                           20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tgaacttgtg gccgtttacg                                           20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgcccgacaa ccactacctg                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ttcagacctt ggctccagat                                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tgaacttgtg gccgtttacg                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ttcagacctt ggctccagat                                           20
```

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
aggctttgga gacagtgagg tgc                                    23

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
taccctcaaa ctcctggtcc ttc                                    23

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gcctgtatgt aatgcctgcg                                        20

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
ccgagcagga atttgaagag g                                      21

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ttacctggcg gacaagagct                                        20

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
ccaatttaga ggagccccac a                                      21

<210> SEQ ID NO 19
<211> LENGTH: 20
<212> TYPE: DNA
<213> ORGANISM: Artificial Sequence
<220> FEATURE:

<223> OTHER INFORMATION: Synthetic

<400> SEQUENCE: 19
catgtactct ttcttgctgg                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ggtctcggga aagcagtggc                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gcctgtatgt aatgcctgcg                                                    20

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ccgagcagga atttgaagag g                                                  21

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
atgagggcct ggatcttctt tc                                                 22

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
ggaagagtcg aaggtcttgt tgtc                                               24

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
aaagtcaatg gctcccacga a                                                  21

```
<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
cttcagtctg tacttcactg g                                              21

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
agatcgctca gatcctggaa                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gggttctggc cttaaggaat                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ttacctggcg gacaagagct                                                20

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
ccaatttaga ggagccccac a                                              21

<210> SEQ ID NO 31
<211> LENGTH: 66
<212> TYPE: RNA
<213> ORGANISM: Artificial Sequence
<220> FEATURE:
<223> OTHER INFORMATION: Synthetic

<400> SEQUENCE: 31
agccacaacg ucuauaucau ggccgacaag uuggcuuguc ggccaugaua uagacguugu    60
ggcugu                                                               66

<210> SEQ ID NO 32
<211> LENGTH: 66
<212> TYPE: RNA
<213> ORGANISM: Artificial Sequence
<220> FEATURE:
```

<223> OTHER INFORMATION: Synthetic

<400> SEQUENCE: 32
gcagcucagc cuuaagaaca uguguaagcu uuggagcuua cacauguucu uaaggcugag    60
cugcaa                                                              66

<210> SEQ ID NO 33
<211> LENGTH: 23
<212> TYPE: DNA
<213> ORGANISM: Artificial Sequence
<220> FEATURE:
<223> OTHER INFORMATION: Synthetic

<400> SEQUENCE: 33
aggctttgga gacagtgagg tgc                                           23

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
taccctcaaa ctcctggtcc ttc                                           23

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
gaacctggct aagcttccaa                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
gaagcgacag atggtggtct                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
gatgaagagg acgctttgga                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
gatttcccag caccagaaaa                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gtggaagacc aggacgacga                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
cctactggat gatagtgtgg                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
tccgcctaat gatgaccttc                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
tccctggtct gggttagttg                                          20

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
aaagtcaatg gctcccacga a                                        21

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
cttcagtctg tacttcactg g                                        21

<210> SEQ ID NO 45
<211> LENGTH: 20
<212> TYPE: DNA
<213> ORGANISM: Artificial Sequence
<220> FEATURE:

<223> OTHER INFORMATION: Synthetic

<400> SEQUENCE: 45
ttacctggcg gacaagagct                                           20

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
ccaatttaga ggagccccac a                                         21

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
acgtaaacgg ccacaagttc                                           20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
tgctcaggta gtggttgtcg                                           20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
tccaaggtgt acgtgaagca                                           20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
tggtgtagtc ctcgttgtgg                                           20

<210> SEQ ID NO 55
<211> LENGTH: 3097
<212> TYPE: DNA
<213> ORGANISM: Artificial Sequence
<220> FEATURE:
<223> OTHER INFORMATION: Synthetic

<400> SEQUENCE: 55
ggcgcgcccc aatgtgaaga gcaagcaaga acgctgagt gctgaaagga aagccgtgta      60
taaacagaga cttggcagc aaggtctgac tctttcatgt ctgtagaaag aatggaagag     120
gaaactcaga tcccccactt gacctgaaac ttcccactag agatcgccag ggtctggagg    180
tgcagccgtg gttaaaagat gaataaagtg aaatgaggta aagcctcttt ttggggggg     240 gggatgtctt tagatcagag gatgcccct aagctttccc tccctcccag tctgggtcac     300
cttacagctt cttttgcatt acaatgtcca tggtggaccc tgcaggtggg attaactgtg    360
aattcacagg gctggtgggg cgtgggtgcc gcctgggtgc ctgggagaat aggggtggg     420 tagggtagga ggcttgaggg gggaggagca ggacctaccc tttaaatcta tcgccttgag    480
ccgttggcct tcagataggc tgatttggtt ggtgtcttgc tctttctgtg ggaaggctgc    540
ccggggccgc caccatgaaa aagcctgaac tcaccgcgac gtctgtcgag aagtttctga    600
tcgaaaagtt cgacagcgtc tccgacctga tgcagctctc ggagggcgaa gaatctcgtg    660 cttcagctt cgatgtagga gggcgtggat atgtcctgcg ggtaaatagc tgcgccgatg    720
gtttctacaa agatcgttat gtttatcggc actttgcatc ggccgcgctc ccgattccgg    780
aagtgcttga cattggggaa ttcagcgaga gcctgaccta tgcatctcc cgccgtgcac    840 agggtgtcac gttgcaagac ctgcctgaaa ccgaactgcc cgctgttctg cagccggtcg    900
cggaggccat ggatgcgatc gctgcggccg atcttagcca gacgagcggg ttcggcccat    960
tcggaccgca aggaatcggt caatacacta catggcgtga tttcatatgc gcgattgctg   1020
atccccatgt gtatcactgg caaactgtga tggacgacac cgtcagtgcg tccgtcgcgc   1080
aggctctcga tgagctgatg ctttgggccg aggactgccc cgaagtccgg cacctcgtgc   1140
acgcggattt cggctccaac aatgtcctga cggacaatgg ccgcataaca gcggtcattg   1200
actggagcga ggcgatgttc ggggattccc aatacgaggt cgccaacatc ttcttctgga   1260
ggccgtggtt ggcttgtatg gagcagcaga cgcgctactt cgagcggagg catccggagc   1320
ttgcaggatc gccgcggctc cgggcgtata tgctccgcat tggtcttgac caactctatc   1380
agagcttggt tgacggcaat ttcgatgatg cagcttgggc gcaggtcga tgcgacgcaa   1440 tcgtccgatc cggagccggg actgtcgggc gtacacaaat cgcccgcaga agcgcggccg   1500
tctggaccga tggctgtgta gaagtactcg ccgatagtgg aaaccgacgc cccagcactc   1560
gtccgagggc aaaggaaatg gtgagcaagg gcgaggagct gttcaccggg gtggtgccca   1620

-continued

```
tcctggtcga gctggacggc gacgtaaacg gccacaagtt cagcgtgtcc ggcgagggcg    1680
agggcgatgc cacctacggc aagctgaccc tgaagttcat ctgcaccacc ggcaagctgc    1740
ccgtgccctg gcccaccctc gtgaccaccc tgacctacgg cgtgcagtgc ttcagccgct    1800
accccgacca catgaagcag cacgacttct tcaagtccgc catgcccgaa ggctacgtcc    1860
aggagcgcac catcttcttc aaggacgacg gcaactacaa gacccgcgcc gaggtgaagt    1920
tcgagggcga caccctggtg aaccgcatcg agctgaaggg catcgacttc aaggaggacg    1980
gcaacatcct ggggcacaag ctggagtaca actacaacag ccacaacgtc tatatcatgg    2040
ccgacaagca gaagaacggc atcaaggtga acttcaagat ccgccacaac atcgaggacg    2100
gcagcgtgca gctcgccgac cactaccagc agaacacccc catcggcgac ggccccgtgc    2160
tgctgcccga caaccactac ctgagcaccc agtccgccct gagcaaagac cccaacgaga    2220
agcgcgatca catggtcctg ctggagttcg tgaccgccgc cgggatcact ctcggcatgg    2280
acgagctgta caagtaaagc ggccgcgact ctagatcata atcagccata ccacatttgt    2340
agaggtttta cttgctttaa aaaacctccc acacctcccc ctgaacctga aacataaaat    2400
gaatgcaatt gttgttgtta acttgtttat tgcagcttat aatggttaca aataaagcaa    2460
tagcatcaca aatttcacaa ataaagcatt ttttccactg cattctagtt gtggttaatt    2520
aaggaacgcc tcatcaatgc ctgcagtttt tcatcccgag aactattctt gcttacaagg    2580
gtctgctact gagatgctct gcacagaggc tggtaaggaa ttcagtcccc gaagaaccca    2640
gtaaattagg gtaagagtag aaaaaacggg ctgaagggtt attgcttctt tatgaaccgt    2700
agtagtcatt aacataagcg ggtgtcctta tcactcttct ggaacccct ctgagtttga    2760 ccggtgatac gttggccttc tagtctgaaa tagagatccg ggacacagga cggagcaata    2820
taaggctctt gtgtgtattt gagaacctaa atatttgggc tctttggaat atgttcgggg    2880
gcagtgagtg gtgtcttcag tagcagggag acctaacatc ctagcttgga atgagcaccc    2940
catttttttg gtgaggttat acagttagtt tgcaatttgc ccaaatggcc gttttctcca    3000
gcagaagcag ttagcatttc tctcaacctt tgggaatatg gatgtcactt agcagttctg    3060
ggtttgtgag ctcagtgctc cttccaaacg gccggcc                             3097
```